United States Patent [19]

Shimizu et al.

[11] Patent Number: 5,595,686
[45] Date of Patent: Jan. 21, 1997

[54] SILACYCLOHEXANE COMPOUNDS, A LIQUID CRYSTAL COMPOSITION COMPRISING THE SAME AND A LIQUID CRYSTAL DEVICE COMPRISING THE COMPOSITION

[75] Inventors: Takaaki Shimizu; Takeshi Kinsho; Tsutomu Ogihara; Tatsushi Kaneko; Mutsuo Nakashima, all of Niigata-ken; Hideshi Kurihara, Kawasaki, all of Japan

[73] Assignee: Shin-Etsu Chemical Co., Ltd., Tokyo, Japan

[21] Appl. No.: 523,095

[22] Filed: Sep. 1, 1995

[30] Foreign Application Priority Data

Sep. 2, 1994 [JP] Japan .................................. 6-234243
Nov. 10, 1994 [JP] Japan .................................. 6-301327

[51] Int. Cl.$^6$ .................. C09K 19/34; C09K 19/30; C07F 7/08; G02F 1/13
[52] U.S. Cl. .................. 252/299.61; 252/299.01; 252/299.63; 252/299.64; 252/299.65; 252/299.66; 252/299.67; 556/406; 349/182
[58] Field of Search .................. 252/299.01, 299.61, 252/299.63, 299.64, 299.65, 299.66, 299.67; 556/406; 359/103

[56] References Cited

U.S. PATENT DOCUMENTS

| | | | |
|---|---|---|---|
| 4,229,315 | 10/1980 | Krause et al. | 252/299.63 |
| 4,340,498 | 7/1982 | Sugimori | 252/299.5 |
| 5,454,977 | 10/1995 | Shimizu et al. | 252/299.61 |
| 5,496,501 | 3/1996 | Shimizu et al. | 252/299.61 |
| 5,498,737 | 3/1996 | Ogihara et al. | 556/406 |
| 5,514,824 | 5/1996 | Kinsho et al. | 556/406 |
| 5,519,156 | 5/1996 | Kinsho et al. | 556/406 |
| 5,523,439 | 6/1996 | Ogihara et al. | 556/406 |
| 5,523,440 | 6/1996 | Nakashima et al. | 556/406 |

FOREIGN PATENT DOCUMENTS

| | | |
|---|---|---|
| 0003215 | 8/1979 | European Pat. Off. . |
| 0355008 | 2/1990 | European Pat. Off. . |
| 0665232 | 8/1995 | European Pat. Off. . |
| 59-109576 | 6/1984 | Japan . |
| 62-54783 | 11/1987 | Japan . |
| 1-42260 | 9/1989 | Japan . |
| 1-50691 | 10/1989 | Japan . |
| 1-50694 | 10/1989 | Japan . |
| 2-10820 | 3/1990 | Japan . |
| 2-12211 | 3/1990 | Japan . |
| 2082196 | 3/1982 | United Kingdom . |
| 2094822 | 9/1982 | United Kingdom . |
| WO91/02043 | 2/1991 | WIPO . |

OTHER PUBLICATIONS

Stephen S. Washburne et al, Journal of Organometallic Chemistry, 133, Acetolysis of 4,4-Disubstituted 4-Silacyclohexyl Tosylates: Effect of Remote Silicon Substitution on Organic Reactivity, Elsevier Scquoia S. A., Lausanne, 1977, pp. 7–17.

Raymond A. Felix et al, Journal of Organometallic Chemistry, vol. 37, No. 14, Preparation and Spectral Properties of β–Silyl–Substituted α,β–Unsaturated Ketones, 1972, pp. 2323–2327.

Jikken Kagaku Koza (Experimental Chemical Course), fourth edition, vol. 26, pp. 159–266, published by Maruzen K. K.

Primary Examiner—Shean C. Wu
Attorney, Agent, or Firm—Lowe, Price, LeBlanc & Becker

[57] ABSTRACT

A silacyclohexane compound of the following formula (I)

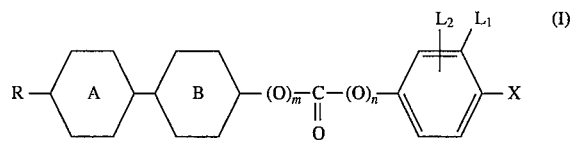

wherein R represents an organic residue; at least one of

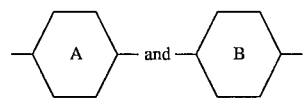

represents a substituted or unsubstituted trans-1-sila-1,4-cyclohexylene group or trans-4-sila-1,4-cyclohexylene group and the other represents a trans-1,4-cyclohexylene group, $L_1$ and $L_2$ independently represent H, F, Cl or $CH_3$; X represents an organic residue or CN, F, Cl; and m and n are, respectively, 0 or 1 provided that m+n=1. Silacyclohexane compounds are useful in liquid crystal compositions and also in liquid crystal devices.

15 Claims, No Drawings

SILACYCLOHEXANE COMPOUNDS, A LIQUID CRYSTAL COMPOSITION COMPRISING THE SAME AND A LIQUID CRYSTAL DEVICE COMPRISING THE COMPOSITION

BACKGROUND OF THE INVENTION

1. Field of the Invention

This invention relates to a novel silacyclohexane compound and also to a liquid crystal composition comprising the compound and a device comprising the composition.

2. Description of the Prior Art

The liquid crystal display devices make use of optical anisotropy and dielectric anisotropy of liquid crystal substances. Depending on the mode of display, a variety of display systems are known including those of a twisted nematic type (TN type), a supertwisted nematic type (STN type), a super birefringence type (SBE type), a dynamic scattering type (DS type), a guest/host type, a type of deformation of aligned phase (DAP type), a polymer dispersion type (PD type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of temperatures working as a liquid crystal and that they be stable against moisture, air, light, heat, electric field and the like. Moreover, the liquid crystal substances should desirably be low in viscosity and should ensure a short address time, a low threshold voltage and a high contrast in cells.

Liquid substances which can satisfy all these requirements have never been known when used as a single compound. In practice, several to ten and several liquid compounds or latent liquid crystal compounds are mixed and used in the form of a mixture. To this end, it is important that constituent components be readily compatible with one another.

Typical of such constituent components are ester compounds having a relatively high nematic-isotropic transition temperature, $T_{NI}$. The ester compounds include those compounds having a phenyl ester structure of bicyclohexylcarboxylic acids of the following formulas.

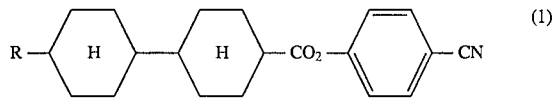
(1)

wherein R represents an alkyl group having from 1 to 8 carbon atoms as set out in Japanese Patent Publication No. 60-17777.

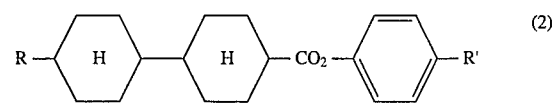
(2)

wherein R represents an alkyl group having from 1 to 8 carbon atoms and R' is an alkyl group or alkanoyloxy group having less than 8 carbon atoms as set out in Japanese Patent Publication No. 60-17777.

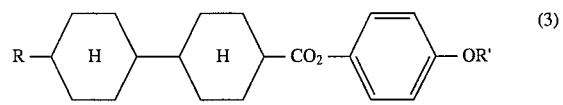
(3)

wherein R and R' are, respectively, an alkyl group having less than 8 carbon atoms as set out in Japanese Patent Publication No. 60-17777.

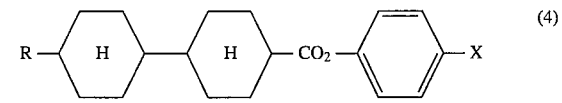
(4)

wherein R is an alkyl group having from 1 to 15 carbon atoms and X is F, Cl or Br as set out in Japanese Patent Publication No. 61-26979.

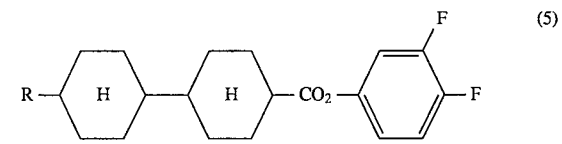
(5)

wherein R is a linear alkyl group having from 1 to 9 carbon atoms as set out in Japanese Patent Publication No. 62-54783.

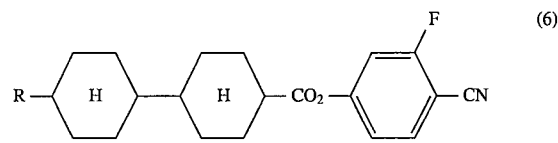
(6)

wherein R is an alkyl group having from 1 to 10 carbon atoms as set out in Japanese Patent Publication No. 1-42260.

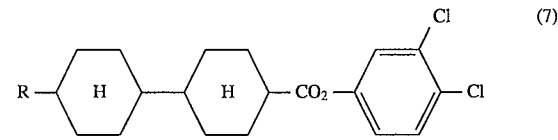
(7)

wherein R is an alkyl group having from 1 to 10 carbon atoms as set out in Japanese Patent Publication No. 1-50691.

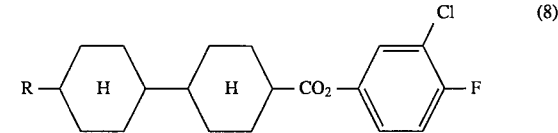
(8)

wherein R is an alkyl group having from 1 to 10 carbon atoms as set out in Japanese Patent Publication No. 1-50694.

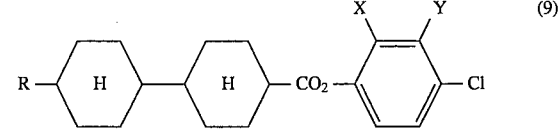
(9)

wherein R is an alkyl group having from 1 to 10 carbon atoms and X and Y are independently H or $CH_3$ as set out in Japanese Patent Publication No. 2-12211.

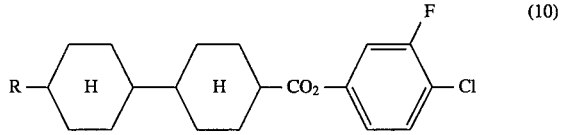
(10)

wherein R is an alkyl group having less than 12 carbon atoms where one or two of the $CH_2$ groups may be replaced by O or CH=CH as set out in Japanese Patent Publication No. 4-501275.

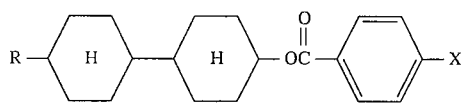

wherein R is an alkyl group having from 1 to 10 carbon atoms and X is R or OR as set out in Japanese Patent Publication No. 2-10820.

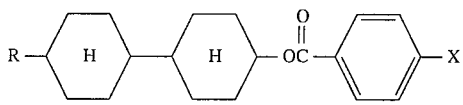

wherein R is an alkyl group having from 1 to 10 carbon atoms and X is F or Cl as set out in Japanese Patent Publication No. 2-10820.

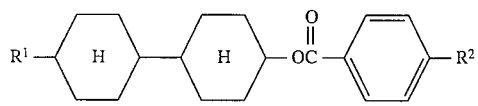

wherein $R^1$ and $R^2$ are, respectively, an alkyl group having from 1 to 10 carbon atoms as set out in Japanese Patent Publication No. 60-17777.

As the liquid crystal display devices recently have wider utility, the characteristic properties required for the liquid crystal materials become severer along with a diversity of drive systems and working modes being in progress. In particular, liquid crystal materials which meet on-vehicle needs should have a nematic phase extended to a high temperature region from the standpoint of use conditions. For the extension of the nematic phase to a high temperature region, it is sufficient to add a liquid crystal compound having a high nematic-isotropic transition temperature, $T_{NI}$, as a constituent component. The known component having a high $T_{NI}$ value includes, for example, 4,4"-substituted terphenyl, 4,4'-substituted biphenylcyclohexane, 4,4'-substituted cyclohexanebiphenylcyclohexane. However, these compounds cause the viscosity of mixed liquid crystal to increase, thus bringing about a response speed being lowered.

SUMMARY OF THE INVENTION

It is an object of the invention to provide a novel compound serving as a liquid crystal substance which has a relatively high nematic-isotropic transition temperature, $T_{NI}$, and does not increase the viscosity of a mixed liquid crystal composition comprising the compound.

It is another object of the invention to provide a novel liquid crystal compound which has such a structure as having never been known in the art and has a silacyclohexane ring containing a silicon atom in the molecule.

It is a further object of the invention to provide a liquid crystal composition which comprise at least compound as set out above and also a liquid crystal display device comprising the composition.

The above object can be achieved, according to the invention, by a silacyclohexane compound of the following formula (I)

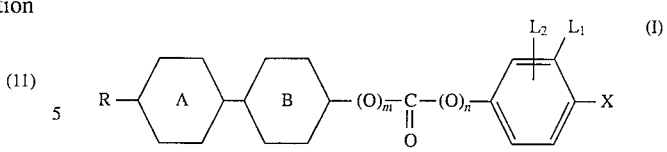

wherein R represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms; at least one of

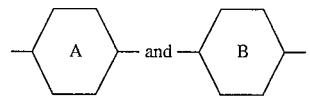

represents a trans-1-sila-1,4-cyclohexylene group or trans-4-sila-1,4-cyclohexylene group in which the silicon atom at the 1 or 4 position has a substituent of H, F, Cl or $CH_3$, and the other represents a trans-1,4-cyclohexylene group, $L_1$ and $L_2$ independently represent H, F, Cl or $CH_3$; X represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY=CX_1X_2$ wherein l is 0 or 1, Y and $X_1$ independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents, H, F or Cl; and m and n are, respectively, 0 or 1 provided that m+n=1.

The compound of the formula (I) includes compounds of the formulas (II) and (III)

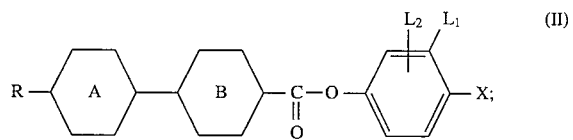

and

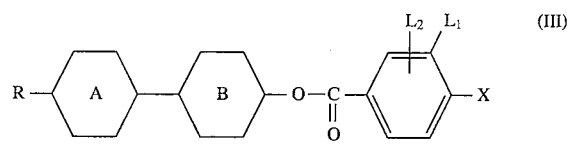

The invention also provides a liquid crystal composition which comprises the silacyclohexane compound of the formula (I). Preferably, the silacyclohexane compound is present in amounts of from 5 to 30 mole % of the composition. In addition, the invention provides a liquid crystal display device comprising a cell structure which comprises the silacyclohexane compound of the formula (I).

Among the compounds of the formula (I) according to the invention, those compounds of the formula (I) wherein X is an alkyl group or an alkoxy group are low in polarity. When these compounds are employed as a constituent component in liquid crystal compositions, the $T_{NI}$ value increases and these tricyclic compounds do not increase a viscosity of the composition on comparison with the afore-mentioned tetracyclic compounds used as the high $T_{NI}$ component. With the compounds of the formula (I) wherein X is a group other than those groups mentioned above, they have an effect of increasing the $T_{NI}$ value and have a dielectric anisotropy (Δε) which is either positive or negative. As a result, the compounds serve to low the drive voltage and ensure a high response speed.

DETAILED DESCRIPTION OF THE INVENTION

The novel compounds of the invention serving as a liquid crystal are those of the formula (I) indicated hereinbefore. More specifically, the compounds have novel ring structures including a trans-1-silacyclohexane ring or a trans-4-silacyclohexane ring and include, for example, the compounds of the following formulas (IV) to (XI):

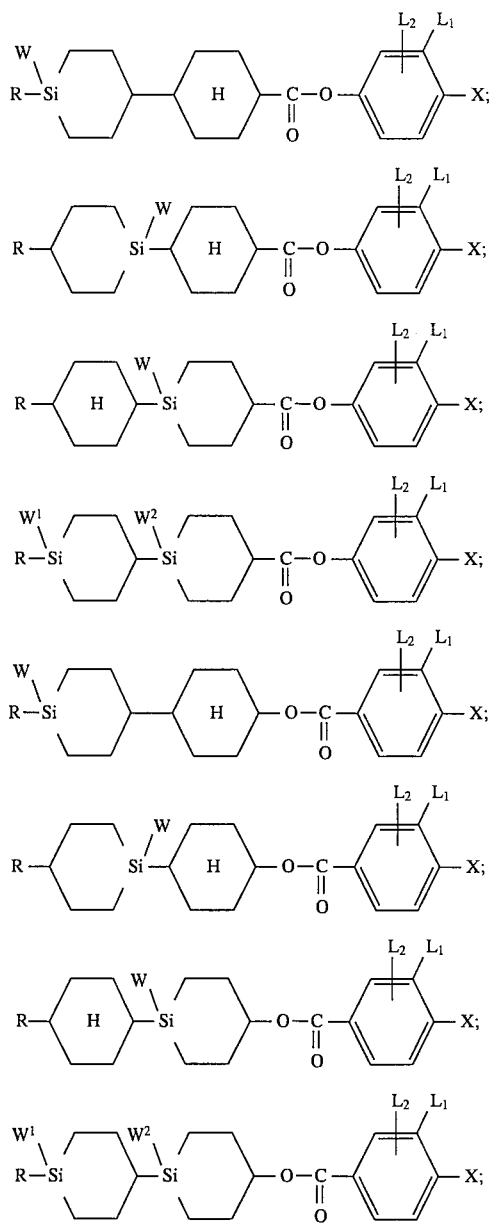

In the formulas (IV) to (XI), R represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms, X represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY=CX_1X_2$ wherein l is 0 or 1, Y and $X_1$ independently represent H, F or Cl, $H_2$ represents F or Cl, or $O(CH_2)_r(CF_2)_sX_3$ wherein r and s are, respectively, 0, 1 or 2 provided that r+s=2, 3 or 4, $X_3$ represents H, F or Cl, W, $W^1$ and $W^2$ independently represent H, F, Cl or $CH_3$, and $L_1$ and $L_2$ independently represent H, F, Cl or $CH_3$.

Specific examples of the linear alkyl group having from 1 to 10 carbon represented by R include methyl, ethyl, n-propyl, n-butyl, n-pentyl, n-hexyl, n-heptyl, n-octyl, n-nonyl and n-decyl. Specific examples of the branched alkyl group having 3 to 8 carbon atoms represented by R include isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl. Specific examples of the mono or difluoroalkyl group having from 1 to 10 carbon atoms represented by R include fiuoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-difluorohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Specific examples of the alkoxyalkyl group having from 2 to 7 carbon atoms represented by R include methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl. butoxypropyl, methoxybutyl, ethoxybutyl, propoxybutyl, methoxypentyl and ethoxypentyl. Specific examples of the alkenyl group having from 2 to 8 carbon atoms represented by R include vinyl, 1-propenyl, allyl, 1-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl and 7-octenyl.

Examples of the linear alkyl group represented by X are those indicated above with respect to R. Examples of the linear alkoxy group having from 1 to 10 carbon atoms represented by X include methoxy, ethoxy, n-propoxy, n-butoxy, n-pentoxy, n-hexyloxy, n-heptyloxy, n-octyloxy, n-nonyloxy and n-decyloxy. Examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl, ethoxypentyl and methoxyhexyl.

The silacyclohexane compound of the formula (I) has a moiety of the following formula (1)

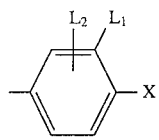

(1)

Specific examples of the moiety include residues of the following formulas

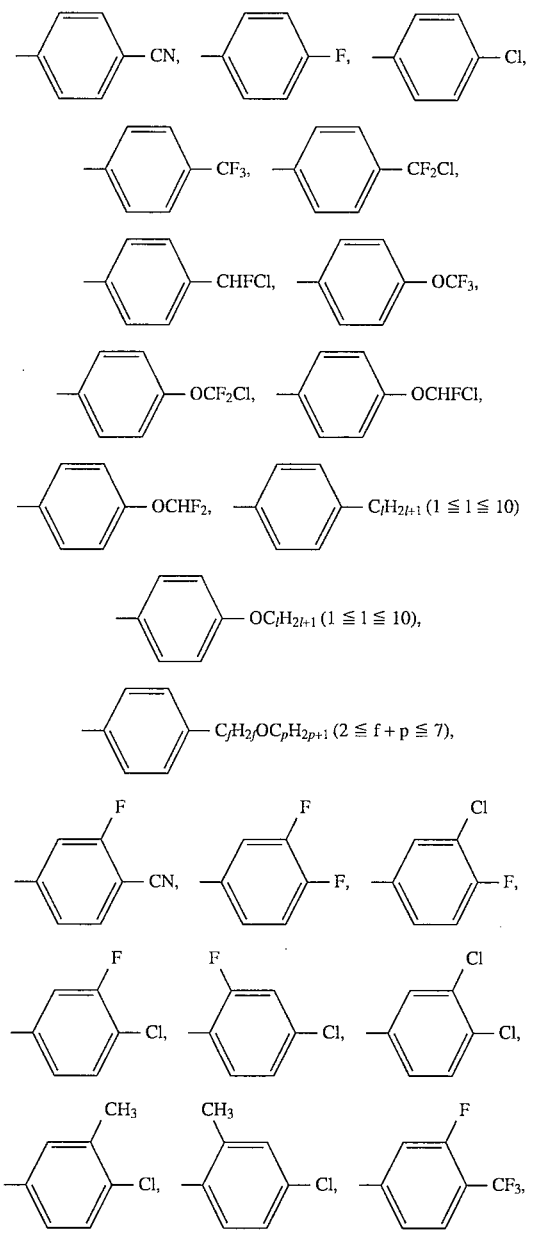

-continued

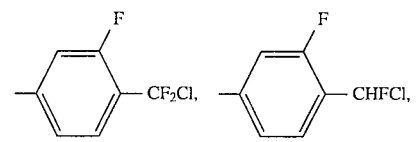

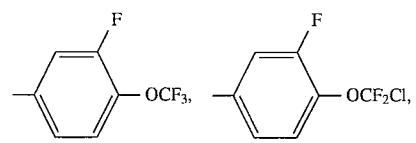

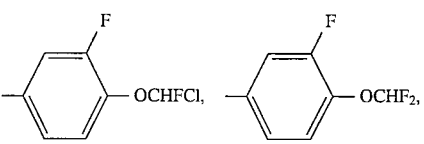

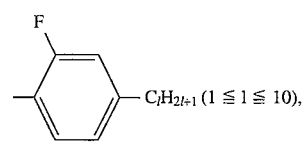

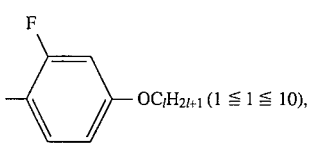

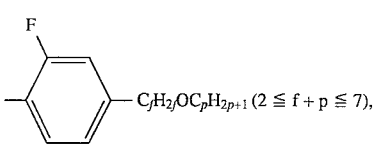

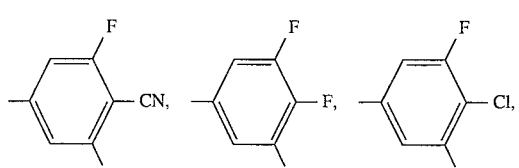

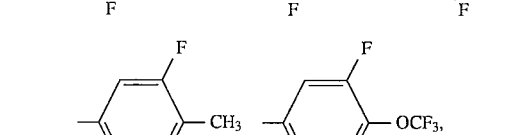

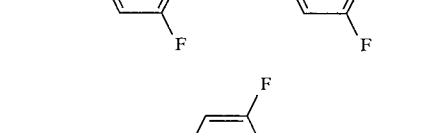

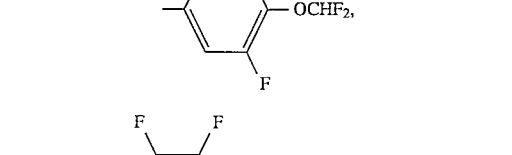

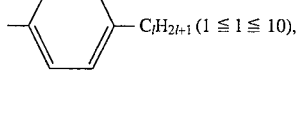

-continued

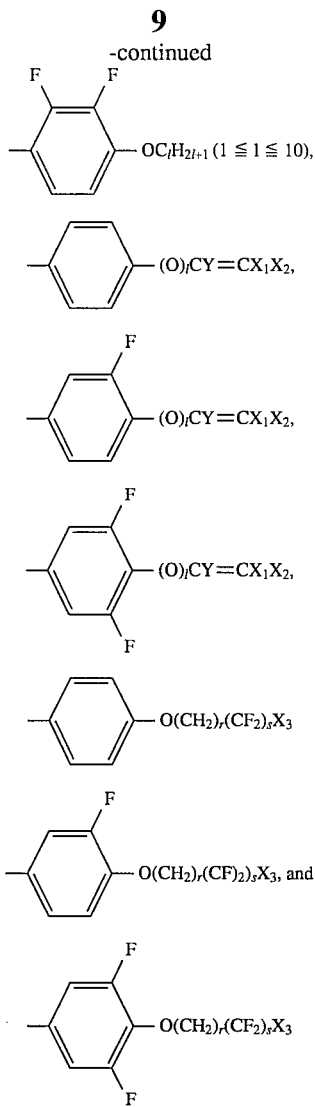

wherein Y, $X_1$, $X_2$, $X_3$, l, r and s are, respectively, as defined hereinbefore.

Preferred silacyclohexane compounds include those of the afore-indicated formulas (IV), (VI), (VIII) and (X) shown below:

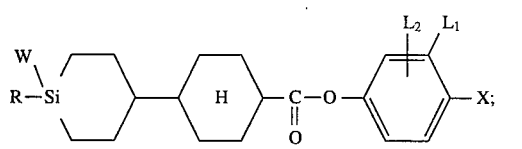
(IV)

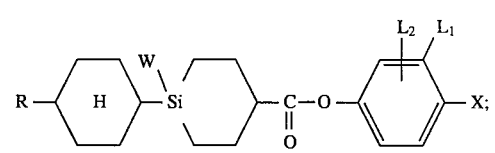
(VI)

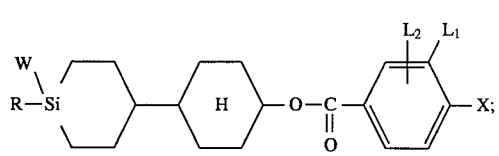
(VIII)

and

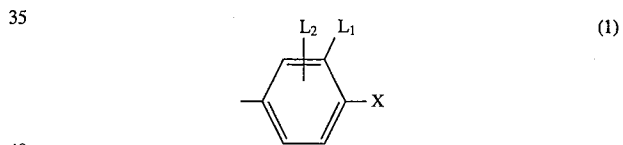
(X)

Preferred groups represented by R include: linear alkyl groups having from 2 to 7 carbon atoms, e.g. ethyl, n-propyl, n-butyl, n-pentyl, n-hexyl and n-heptyl; mono or difluoroalkyl groups having from 2 to 7 carbon atoms, such as 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluoroheptyl, 6-fluorohexyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl; branched alkyl groups having from 3 to 8 carbon atoms, such as isopropyl, 1-methylpentyl, 2-methylpentyl, 1-methylbutyl, 2-methylbutyl, 3-methylbutyl, 1-methylpentyl, 2-methylpentyl and 2-ethylhexyl; alkoxyalkyl groups having from 2 to 6 carbon atoms, such as methoxymethyl, methoxyethyl, methoxypropyl, methoxypentyl, ethoxymethyl, ethoxyethyl, propoxymethyl and pentoxymethyl; and alkenyl groups having from (2) to (8) carbon atoms, such as vinyl group, 1-propenyl group, 3-butenyl group, 1-pentenyl group, 3-pentenyl group, 4-pentenyl group, 1-hexenyl group, 5-hexenyl group, 6-heptenyl group and 7-octenyl group.

Preferred atoms or groups represented by W include H, F or $CH_3$.

Preferred moieties represented by the formula (1)

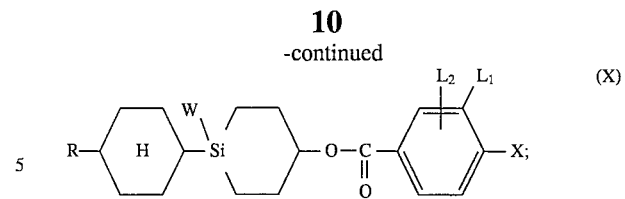
(1)

are those indicated below

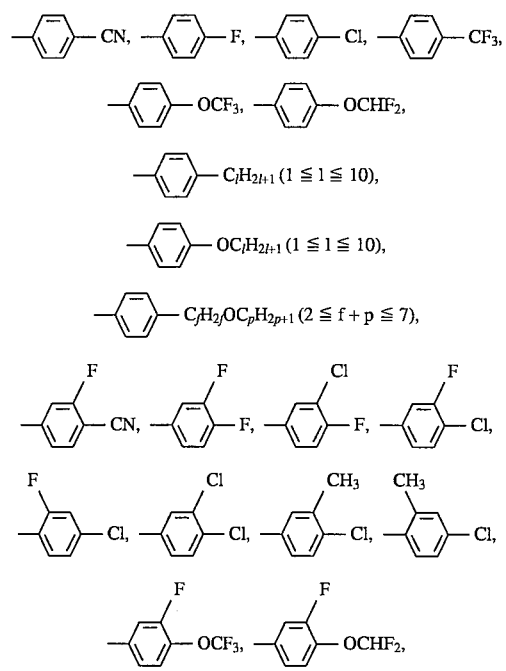

-continued

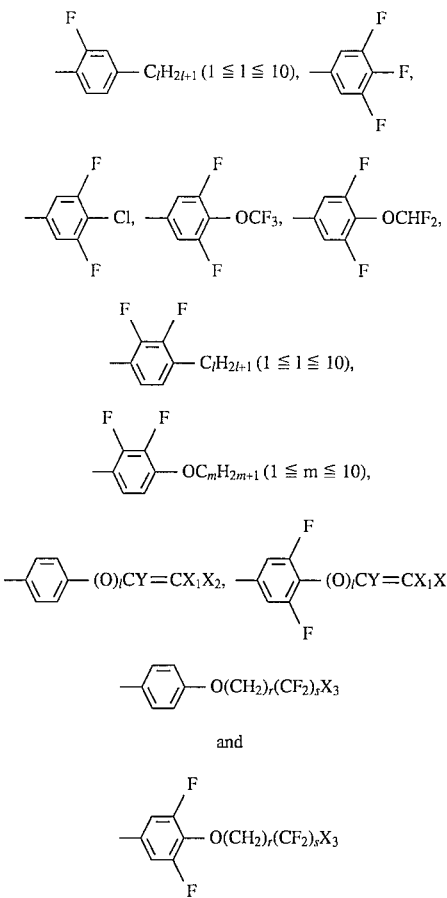

Of these, the compounds having the moieties of the following formulas exhibit a value of Δε close to zero

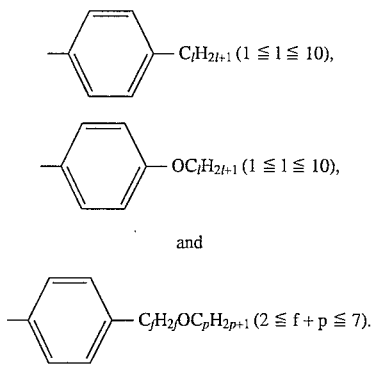

Moreover, the compounds having moieties of the following formulas exhibit a negative value of Δε

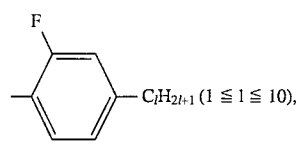

-continued

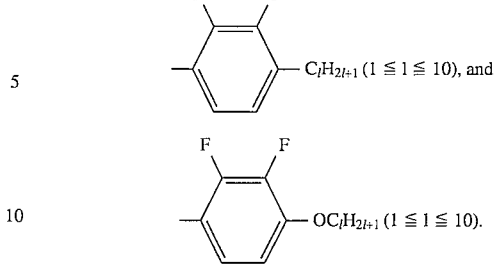

These compounds are suitable for use in DS mode, DAP mode or GH mode display devices.

The preparation of the silacyclohexane compound of the formula (I) according to the invention is now described. The silacyclohexane compounds of the formula (I) differ in manner of preparation depending on the type of substituent joined to the silicon atom of the silacyclohexane ring.

With the methylsilacyclohexane compounds of the following formulas (IV) to (VII) wherein the substituents bonded to the silicon atom or atoms of the silacyclohexane ring or rings are, respectively, a methyl group, i.e. W, $W_1$ and/or $W_2$ is each a methyl group in the formulas,

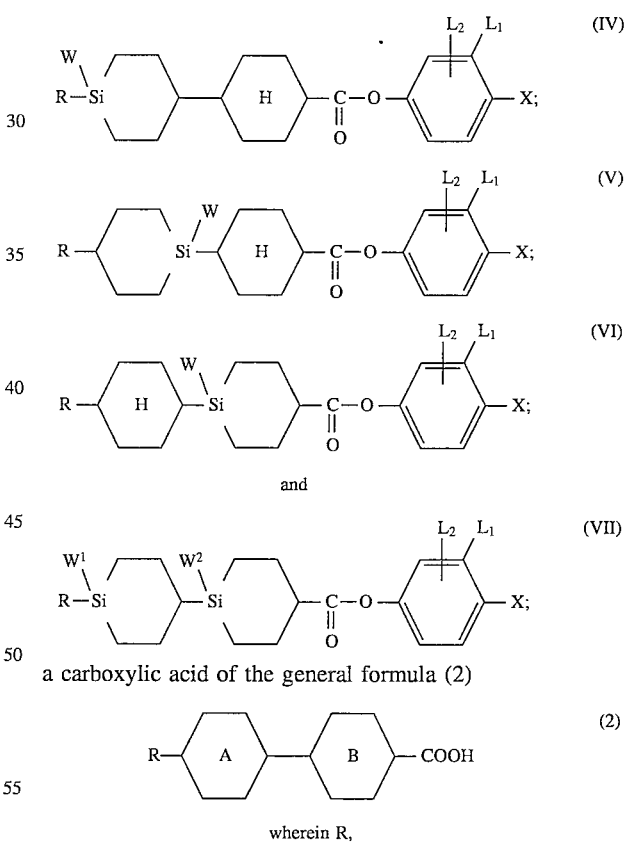

have, respectively, the same meanings as defined hereinbefore, is reacted with a phenol compound of the following general formula (3) through esterification or dehydration and condensation

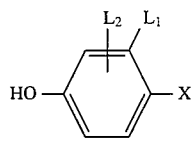

wherein X, $L_1$ and $L_2$ have, respectively, the same meanings as defined hereinbefore.

The esterification reactions include (1) a method wherein the two compounds are condensed by use of dehydrators and (2) a method wherein the carboxylic acid is first converted to an acid chloride and then reacted with the phenol compound in the presence of bases.

The dehydrators used in the method (1) include, for example, diimides such as N, N'-dicyclohexylcarbodiimide, acid anhydrides such as trifluoroacetic anhydride, carbonyldiimidazole, 2-chloropyridinium salts, 3-chloroisooxazolium salts, and combinations of 2,2'-dipyridyldisulfide and phosphines such as methyl phosphine.

In this case, the reaction is preferably effected under conditions of a temperature of from 0° to 100° C. for a time of from 0.5 to 10 hours in a solvent inert to the reaction. Examples of the solvent include carbon tetrachloride, methylene chloride, aromatic hydrocarbons such as benzene, toluene, xylene and the like, and ethers such as tetrahydrofuran.

The reagents used to convert the carboxylic acid to a corresponding an acid chloride in the method (2) include thionyl chloride, phosphorus pentachloride, oxalyl chloride, and combinations of carbon tetrachloride and phosphines. This reaction proceeds by a usual manner preferably under conditions of a temperature ranging from 0° to 100° C. The acid chloride is then reacted with the phenol compound in the presence of bases. Examples of the base include pyridine, 4-dimethylaminopyridine, N,N-dimethylaniline, triethylamine, tetramethylurea and the like. This reaction proceeds readily under normal temperature and pressure conditions.

Moreover, the compounds of the formulas (IV) to (VII) wherein W, $W_1$ and/or $W_2$ is each chlorine, fluorine or hydrogen, (i.e. the atom or substituent joined to the silicon atom or atoms of the silacyclohexane ring or rings is chloride, fluorine or hydrogen), include chlorosilacyclohexane, fluorosilacylohexane and hydrosilacyclohexane compounds. For the preparation of these compounds, arylsilacyclohexane compounds wherein an aryl group such as phenyl or tolyl is attached to each silicon atom of the silacyclohexane ring or rings are used as an intermediate for preparing the chlorosilacyclohexane, fluorosilacylohexane and hydrosilacyclohexane compounds. The arylsilacyclohexane compounds are those compounds of the general formula (IV) to (VII) wherein W, $W_1$ and/or $W_2$ are each an aryl group such as phenyl or tolyl.

These arylsilacyclohexane intermediate compounds are prepared through esterification or dehydration and condensation between corresponding carboxylic acids and phenol compounds, like the compounds of the formulas (IV) to (VII) wherein W, $W_1$ and/or $W_2$ are each $CH_3$.

The conversion of the arylsilacyclohexane intermediate compound to an intended chlorosilacyclohexane, fluorosilacylohexane or hydrosilacyclohexane compound is carried out according to the following reaction sequence wherein only the moiety taking part in the conversion reaction is shown

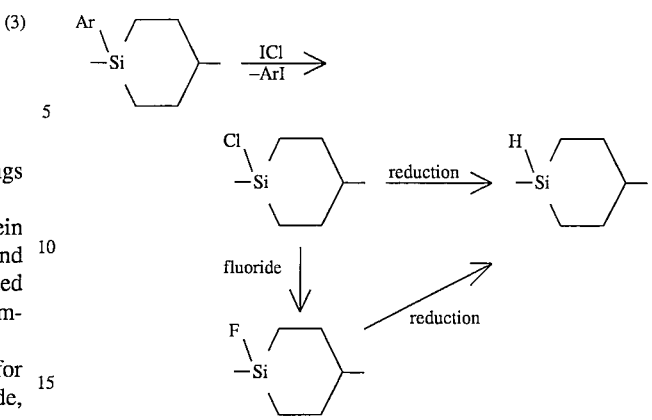

wherein Ar represents a phenyl or tolyl group.

As will be apparent from the above reaction sequence, when iodine monochloride is reacted with the arylsilacyclohexane compound, a chlorosilacyclohexane compound is obtained through the halo de-silylation reaction. The de-silylation reaction may be caused in a wide range of temperatures. Preferably, the temperature used is in the range of from 0° to 80° C., more preferably from 10° to 40° C.

When the resultant chlorosilacyclohexane compound is reacted with fluorides such as cesium fluoride, copper (I) fluoride, antimony fluoride, calcium fluoride, tetra-n-butylammonium fluoride and the like, a fluorosilacyclohexane compound of the formulas (IV) to (VII) wherein W, $W_1$ and/or $W_2$ is each fluorine.

When the chlorosilacyclohexane or fluorosilacyclohexane compound is reacted with a reducing agent under mild conditions not permitting the ester to be reduced, a hydrosilacyclohexane compound of the formulas (IV) to (VII) wherein W, $W_1$ and/or $W_2$ is hydrogen is obtained. Examples of the reducing agent include metal hydrides such as sodium hydride, calcium hydride, trialkylsilanes, boranes, dialkyl aluminium compounds and the like, and complex hydrides such as lithium aluminium hydride, sodium borohydride, lithium borohydride, potassium borohydride, tributylammonium borohydride and the like. Although not limitative, the reduction of the halosilacyclohexane is carded out preferably at a temperature of from −50° to 100° C., more preferably from −20° to 70° C.

If the thus obtained product is in the form of steric isomers, a trans, trans isomer is isolated and purified through known purification procedures such as recrystallization, chromatography and the like.

The starting carboxylic acid of the formula (2) is a novel intermediate and the prepartion thereof is described.

The manner or process of preparing the carboxylic acid of the formula (2) differs depending on the type of substituent represented by W, $W^1$ and/or $W^2$ in the formulas (IV) to (VII) and the type of silacyclohexane compound.

(A) The preparation of the carboxylic acid of the formula (2) where the substituent is a methyl group, i.e. W, $W^1$ and/or $W^2 = CH_3$, is described for different types (a) to (d) of silicon-containing carboxylic acids.

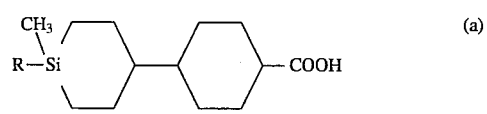

wherein R is as defined with respect to the formula (I).

This type of silacyclohexane compound is prepared from a silacyclohexanone compound of the following formula (a-1)

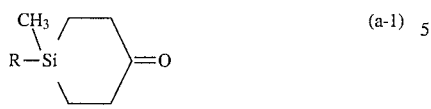

The silacyclohexanone of the formula (a-1) and the preparation thereof are set out in our Japanese Patent Application No. 6-78125, filed Mar. 24, 1994 (corresponding to U.S. patent application Ser. No. 408961, filed Mar. 23, 1995) and also in Journal of Organometal Chem., Vol. 133 (1) pp. 7 to 17 (1977) and Journal of Organometal Chem. Vol. 37 (4), pp. 2323 to 2327 (1972).

The preparation of the compound of the above formula (a) comprises the steps of: coupling of the silacyclohexanone with an organometallic compound; dehydrogenation reaction and hydrogenation or hydrogenolysis; removal of a protective group; hydrogenation of the phenyl group; oxidation of the resultant secondary alcohol; Wittig reaction for conversion to a corresponding aldehyde; and oxidation of the aldehyde to obtain a compound of the formula (a). This reaction sequence (a-2) is shown below.

Ti and Zn-containing reagents. The coupling reaction is usually effected in solvents including ethers such as diethyl ether, tetrahydrofuran, dioxane and the like, and hydrocarbons such as benzene, toluene, xylene, mesitylene, hexane, heptane, octane and the like. These solvent may be used singly or in combination.

(2) The resultant alcohol is then subjected to hydrogenolysis to obtain a cyclohexylphenol compound. Alternatively, the alcohol is first dehydrated with an acid catalyst and then the resultant double bond is hydrogenated to obtain the cyclohexylphenol compound. The hydrogenolysis or hydrogenation reaction is carried out at a temperature of from 0° to 150° C., preferably from 20° to 100° C. at a pressure ranging from an atmospheric pressure to 20 kg/cm$^2$.

The catalysts used for the hydrogenolysis or hydrogenation include palladium, platinum, rhodium, nickel, ruthenium and the like metals. Preferably, these metals are used in the form of combinations or oxides such as palladium-carbon, palladium-barium sulfate, palladium-diatomaceous earth, platinum oxide, platinum-carbon, rhodium-carbon, Raney nickel, palladium oxide, nickel-diatomaceous earth and the like. More preferably, palladium or nickel catalysts are used.

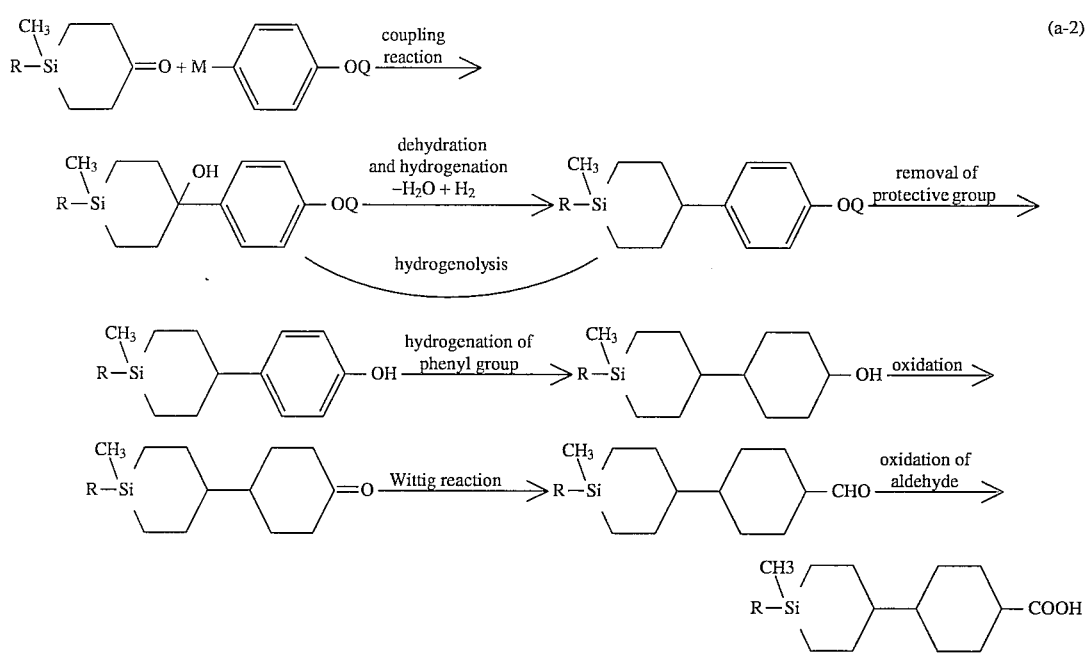

In the above reaction sequence (a-2), X is a protective group including a t-butyldimethylsilyl group, an alkoxymethyl group such as a methoxymethyl group, a benzyl group or the like, and M represents a metal derived from organometallic compounds.

(1) In the first step, the silacyclohexanone is coupled with an organometallic reagent or compound. Examples of the organometallic reagent include Grignard reagents, organozinc reagents, organolithium reagents, organotitanium reagents and the like. Using any of the reagents, the reaction proceeds in high yield. Although depending on the type of organometallic reagent, the reaction is conducted under conditions of a temperature of −70° C. to 150° C. and a time of 30 minutes to 5 hours. More particularly, the reaction temperature ranges from −70° C. to 0° C. for organolithium reagents and from room temperature to 150° C. for the Mg, The acids used for the dehydration include inorganic acids such as hydrochloric acid, sulfuric acid, nitric acid, perchloric acid and the like, and organic acids such as p-toluenesulfonic acid, camphorsulfonic acid, trifluoroacetic acid and the like. In order to quickly remove the resultant water, hydrocarbon solvents such as benzene, toluene, xylene, cumene, hexane, iso-octane and the like are used to permit the reaction to proceed more rapidly through the azeotropy.

(3) Subsequently, the protective group, X, is removed to obtain a (silacyclohexyl)cyclohexylphenol compound. The protective group may be removed according to any known procedure as set out, for example, Theodora W. Greene and Peter G. M. Wuts, "Protective Groups in Organic Synthesis" John Wiley & Sons. INC.

(4) The resultant phenol compound is hydrogenated to convert the phenyl group into a cyclohexane ring.

This hydrogenation reaction is carried out at a pressure of hydrogen of atmospheric to 250 atms for a time ranging from 0.5 to 20 hours in the presence of a catalyst such as Pt, Rh, Ru or Ni supported on a carrier such as alumina, active carbon, magnesia, molecular sieves or the like. The reaction is usually effected in solvents including water, alcohols such as methanol, ethanol and the like, esters such as ethyl acetate, ethers such as tetrahydrofuran, and hydrocarbons such as cyclohexane, iso-octane and the like. It will be noted that the type of solvent, the hydrogen pressure and the temperature depend greatly on the type of catalyst. For instance, Ni catalysts require high temperature and high pressure conditions although they are inexpensive, resulting in an expensive production apparatus. On the other hand, Rh catalysts are advantageous in that the reaction proceeds at normal temperatures at relatively low pressures of from 1 to 5 atms, but are very expensive although an inexpensive production apparatus may be used.

(5) Thereafter, the secondary alcohol is oxidized with oxidizing agents such as permanganates, chromic acid, oxygen, organic peroxides and the like by a usual manner, thereby obtaining a cyclohexanone compound.

(6) The cyclohexanone compound is subjected to Wittig reaction for conversion into a cyclohexanecarbaldehyde as set out in the afore-indicated Japanese Patent Application No. 6-71825. More particularly, the cyclohexanone compound is subjected to Wittig reaction with a ylide compound obtained from an alkoxymethyltriphenylphosphohium salt by the action of a base to obtain an alkylenol ether, followed by hydrolysis with an acid to obtain the carbaldehyde compound according to the following reaction sequence (a-3)

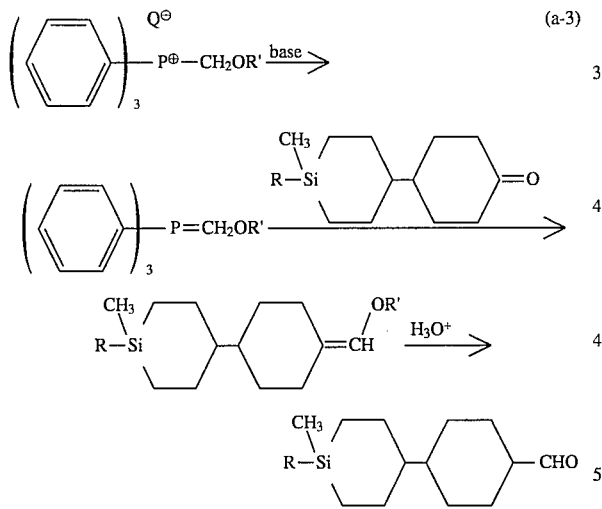

wherein R' is an alkyl group having from 1 to 10 carbon atoms, preferably from 1 to 4 carbon atoms, Q is a halogen, preferably Cl, Br or I.

The alkoxymethyltriphenylphosphonium salts used in the reaction sequence include, for example, methoxymethyltriphenylphosphonium chloride, methoxymethyltriphenylphosphonium bromide, methoxymethyltriphenylphosphonium iodide, ethoxymethyltriphenylphosphonium chloride, ethoxymethyltriphenylphosphonium bromide, ethoxymethyltriphenylphosphonium iodide and the like.

The bases used for the formation of the ylide compound include organolithium compounds such as n-butyl lithium, s-butyl lithium, t-butyl lithium, methyl lithium, phenyl lithium and the like, alkoxides such as sodium methoxide, sodium ethoxide, potassium t-butoxide and the like, dimsyl sodium, and the like. The Wittig reaction is performed in ethers such as tetrahydrofuran, diethyl ether, di-n-butyl ether, 1,4-dioxane and the like, which are used singly or in combination with hydrocarbons such as n-hexane, n-heptane, iso-octane, benzene, toluene, xylene, cumene and the like and aprotic, polar solvents such as N,N-dimethylformamide, dimethylsulfoxide, hexamethylphosphoric triamide and the like. Preferred reaction conditions include a temperature of from 0° C. to a refluxing temperature of the solvent used. The acid catalysts used for the hydrolysis of the alkylenol ether compound include inorganic acids such as hydrochloric acid, sulfuric acid and the like, and organic acids such as acetic acid, oxalic acid, trifluoroacetic acid, chloroacetic acid and the like. The hydrolysis is effected at a temperature of from 0° to 80° C., preferably from 10° to 40° C.

(7) Finally, the carbaldehyde compound is oxidized to obtain the intended carboxylic acid of the formula (2).

Alternatively, the carboxylic acid of the formula (2) may be obtained from the cyclohexanone of the formula (a-1) according to the following reaction sequence (a-4)

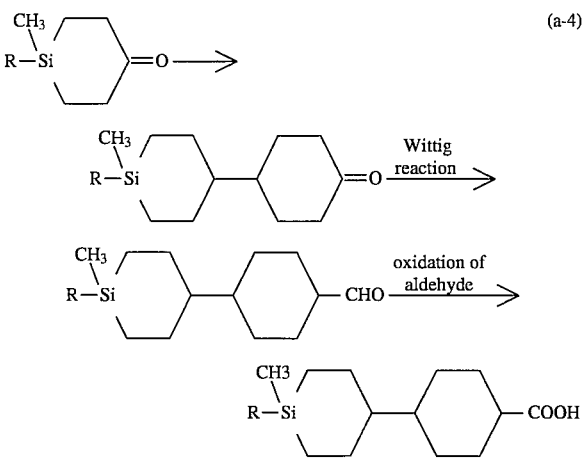

In this reaction sequence, the starting silacyclohexanone is converted to a silacyclohexylcyclohexanone. This conversion reaction is feasible according to a procedure set out in our Japanese Patent Application No. 6-154219, filed Jun. 13, 1994.

Then, the steps (6) and (7) of (a) are repeated to obtain an intended carboxylic acid.

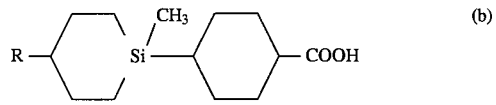

This type of acid compound is prepared from a silacyclohexanone compound of the following formula (b-1)

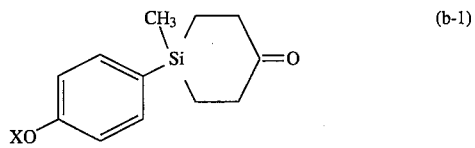

wherein X is a protective group as used in 1-(a) above.

This substituted silacyclohexanone compound (b-1) is prepared in a manner as set forth in (a).

The compound of the formula (b) is prepared by a process which comprises the steps of: coupling reaction with an organometallic compound; dehydration and hydrogenation or Wittig reaction and hydrogenation to obtain an alkylsilacyclohexane compound; removal of the protective group; hydrogenation of the aromatic ring; oxidation of the resultant secondary alcohol, followed by Wittig reaction and oxidation of the resultant aldehyde. The reaction sequence (b-2) is shown below.

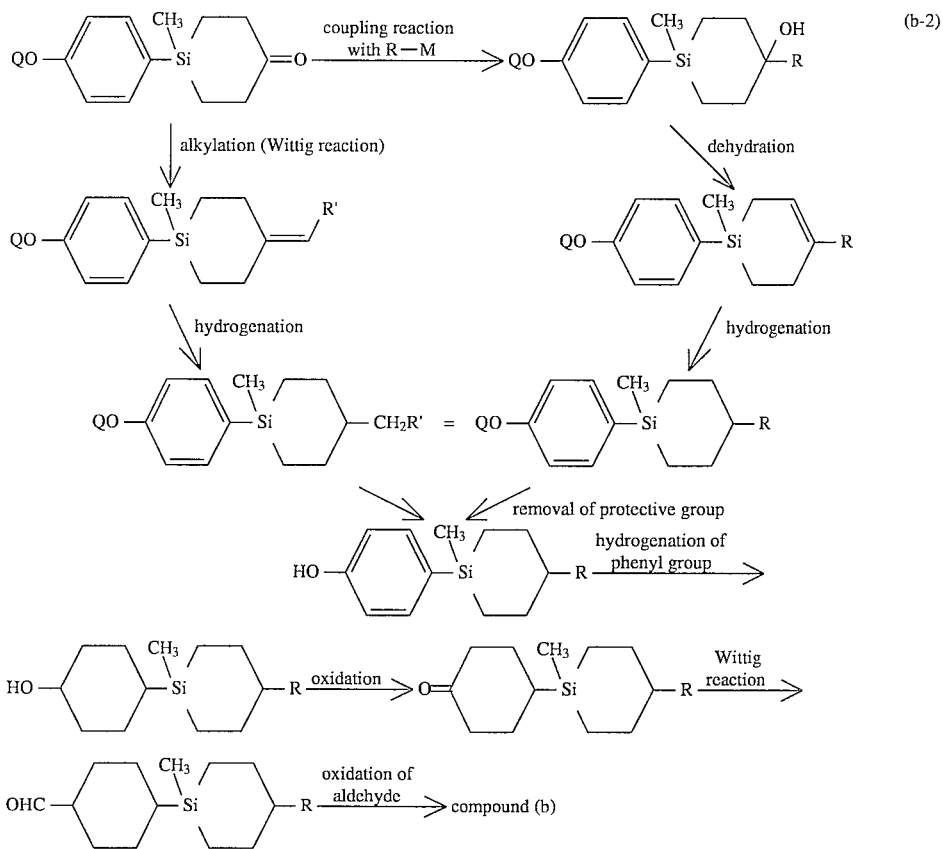

wherein R is a group as defined in the formula (I) and is equal to —CH$_2$R', and Q is a protective group as in (a).

(1) The silacyclohexanone is converted to an alkylsilacyclohexane compound through two ways. One way includes coupling reaction with an organometallic compound, R-M, followed by dehydration and hydrogenation. The other way includes the alkylation reaction and hydrogenation. The dehydration and hydrogenation reaction conditions and reagents used are those as in (a)

The coupling reaction with an organometallic compound, R-M, is carried out in the same manner as in (6) of (a). This reaction is performed in solvents under conditions of a temperature of 0° to 100° C. or a refluxing temperature of a solvent used and a time of from 0.5 to 10 hours. Examples of the solvents include ethers such as ether, tetrahydrofuran and the like, and hydrocarbons such as benzene, toluene, hexane, cyclohexane, iso-octane and the like.

The alkylation reaction is effected under similar conditions as the Wittig reaction set out hereinbefore in (a).

(2) Then, the protective group, Q, is removed from the compound obtained above in the same manner as in (3) of (a), thereby obtaining a silacyclohexylphenol compound.

(3) The resultant phenol compound is hydrogenated to convert the phenyl group into a cyclohexane ring in the same manner as in (4) of (a), followed by repeating the steps of (a).

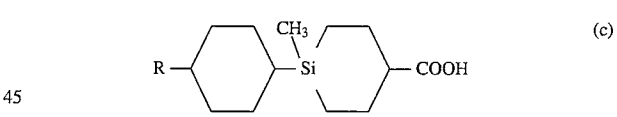

This type of carboxylic acid is prepared from a silacyclohexanone compound of the following formula (c-1)

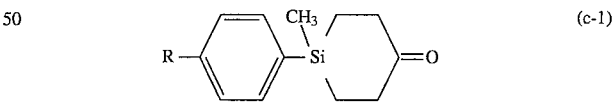

This starting compound is prepared as set out in (a) above.

Using the compound (c-1), the carboxylic acid of the formula (c) is prepared by a process which comprises the steps of: hydrogenation of the aromatic group or ring; Wittig reaction; and oxidation of the resultant aldehyde. This reaction sequence (c-2) is shown below.

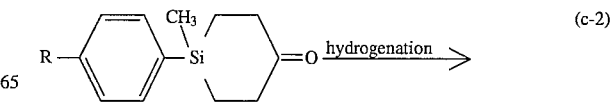

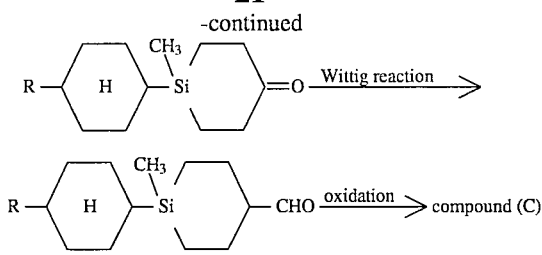

The hydrogenation of the aromatic ring, Wittig reaction and oxidation of the aldehyde are, respectively, conducted in the same manner as in (a) and (b) set out hereinabove.

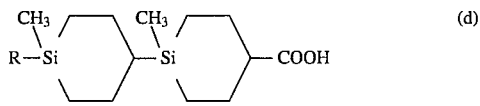

This type of carboxylic acid is prepared from a silacyclohexanone compound of the formula (d-1)

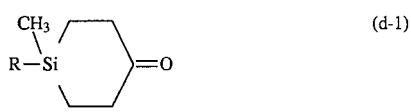

Using the silacyclohexanone compound (d-1), the compound (d) is prepared according to a process which comprises the steps of: reduction of the ketone; halogenation of the resultant secondary alcohol; coupling reaction of the resultant compound with a metal such as Mg or Li and then with a chlorosilane; allylation or vinylation; conversion to a silacyclohexanone compound; and oxidation into a carboxylic acid (d). This reaction sequence (d-2) is shown below.

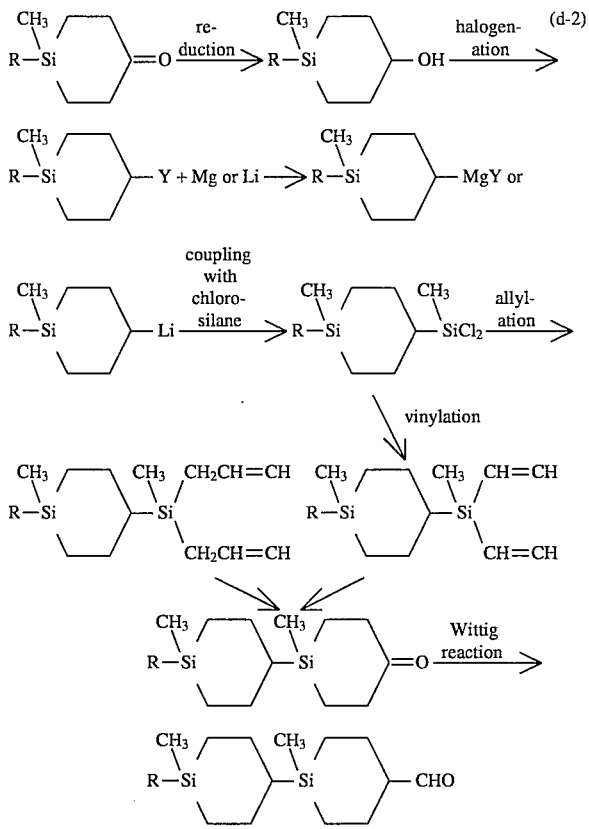

In the above reaction sequence (d-2), Y represents a halogen such as Cl, Br or the like.

(1) The starting silacyclohexanone compound is reduced any known procedures as set out, for example, in Jikken Kagaku Koza (Experimental Chemical Course), fourth edition, Vol. 26, pp. 159 to 266 (1992), published by Maruzen K.K.

(2) The resultant secondary alcohol is halogenated with a halogenating agent such as thionyl chloride, phosphorus pentachloride or phosphorus tribromide or combinations of halogenating agents and phosphines. Examples of the halogenating agents used in the combination include $CCl_4$, N-bromosuccinimide, bromine and the like and examples of the phosphines include triphenylphosphine, trialkylphosphines and the like. This reaction is carried out in solvents such as halogenated hydrocarbons, dimethylformamide, tetrahydrofuran, acetonitrile and the like at a temperature of from 0° to 100° C., preferably from 5° to 80° C., for a time of 0.5 to 20 hours.

(3) The thus halogenated compound is coupled with a chlorosilane in the presence of a metal such as Li or Mg. The reaction is effected in solvents such as ethers such as ethyl ether, tetrahydrofuran and the like or hydrocarbons such as benzene, toluene, hexane, cyclohexane, iso-octane and the like. The reaction conditions include a temperature of from 20° to 100° C. for the reaction with the metal, a temperature from 0° to 100° C. for the coupling reaction with the chlorosilane and a time of 0.5 to 10 hours for both cases.

(4) The thus coupled compound is allylated with an allylating agent such as allyl chloride or allyl bromide in the presence of Li or Mg in the same manner as in (3) of (d) above using similar solvents and reaction conditions. Altenatively, the coupled compound may be vinylated with vinyl chloride or vinyl bromide in the same manner as for the allylation.

(5) The allylated compound is converted to a silacyclohexanone in a manner as set out in our Japanese Patent Application No. 6-78125, filed Mar. 24, 1994. The vinylated compound is converted to a silacyclohexanone in a manner as set out in our Japanese Patent Application No. 7-72417, filed Mar. 6, 1995.

(6) The silacyclohexane is then converted to a corresponding aldehyde through Wittig reaction as set out in (a) to (c), followed by oxidation to obtain a corresponding carboxylic acid.

(B) The preparation of the carboxylic acid of the formula (2) where the substituent is F, Cl or H, i.e. W, $W^1$ and/or $W^2$ =F, Cl or H, is described for different types (a') to (d') of silacyclohexane compounds. It will be noted that because the conversion of an arylsilacyclohexane to chlorosilacyclohexane, fluorosilacyclohexane and hydrosilacyclohexane has been described hereinbefore, preparation of different types of arylsilacyclohexane compounds is described below.

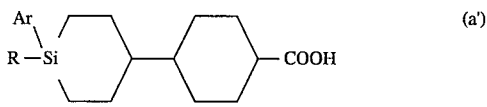

wherein Ar is an aryl group.

This type of carboxylic acid is obtained from a corresponding aldehyde according to the following reaction formula (a'-1)

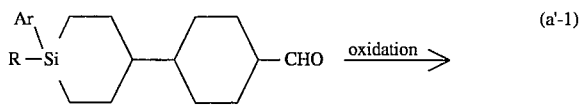

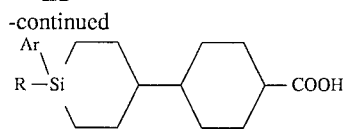

The aldehyde compound is prepared in a manner as set out in our Japanese Patent Application No. 6-182904, filed Jul. 12, 1994 and thus not yet laid open. The oxidation of the aldehyde is as set out in (A) above.

The compound of the formula (b') is prepared by a process which comprises the steps of: coupling reaction with an organometallic compound; dehydration and hydrogenation or Wittig reaction and hydrogenation; removal of a protective group; hydrogenation of the phenyl group; oxidation of the resultant secondary alcohol, followed by Wittig reaction and oxidation of the resultant aldehyde.

The reaction sequence (b'-2) is shown below.

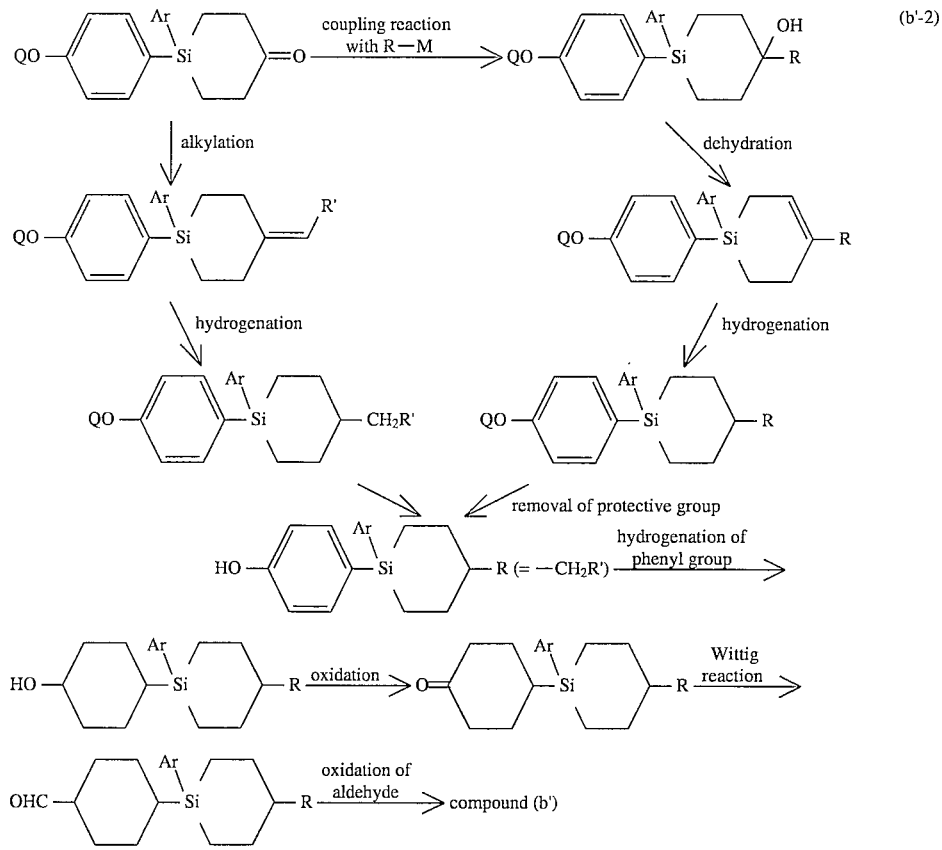

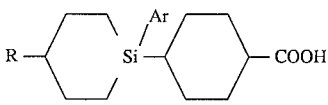

This type of silacyclohexane compound is prepared from a silacyclohexanone compound of the following formula (b'-1)

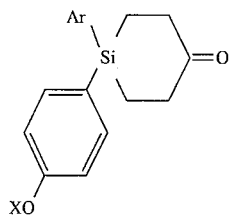

wherein X is a protective group as defined in (A)–(a).
This substituted silacyclohexanone compound (b'-1) is prepared in a manner as set forth in (A)–(a).

wherein R and R' are as defined hereinbefore, respectively, and Q is a protective group as in (a').

These reaction steps can be conducted in the same manner as in (b) of (A) except that the starting material differs from that of (b).

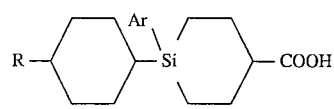

This type of carboxylic acid is prepared from a silacyclohexanone compound of the following formula (c'-1)

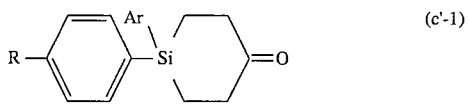

This starting compound is prepared as set out in (a) of (A).

Using the compound (c'-1), the carboxylic acid of the formula (c') is prepared in the same manner as in (c) of (A) set out hereinbefore, as comprising the steps of: hydrogenation of the aromatic ring; Wittig reaction; and oxidation of the resultant aldehyde.

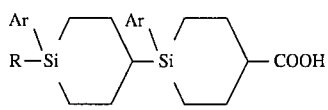 (d')

This type of carboxylic acid is prepared from a silacyclohexanone compound of the formula (d'-1)

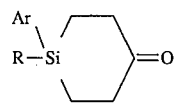 (d'-1)

Using the silacyclohexanone compound (d'-1), the compound (d') is prepared in the same manner as in the process set out in (d) of (A) hereinbefore.

The preparation of the silacyclohexane compounds of the formulas (IV) to (VII) has been described hereinabove along with the preparation of the starting carboxylic acid of the formula (2).

On the other hand, the silacyclohexane compounds of the following formulas (VIII) to (XI) may be likewise prepared from carboxylic acids and secondary alcohols

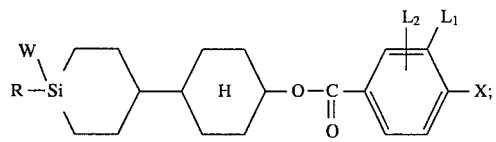 (VIII)

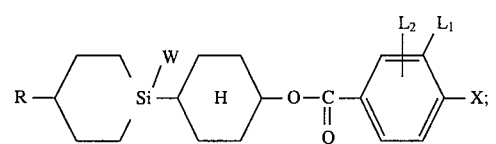 (IX)

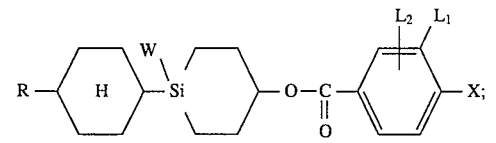 (X)

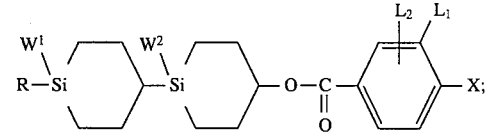 (XI)

More particularly, when a carboxylic acid of the following general formula (4)

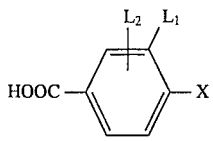 (4)

wherein X, $L_1$ and $L_2$ have, respectively, the same meanings as defined hereinbefore, is reacted with a secondary alcohol of the following general formula (5)

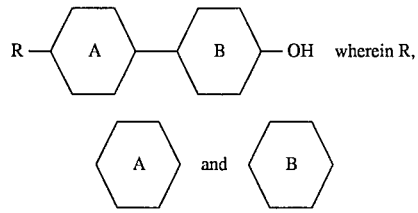 (5)

have, respectively, the same meanings as defined hereinbefore, the silacyclohexane compounds of the formulas (VIII) to (XI) are prepared. Similar esterification reaction conditions and reagents as used in the methods (1) and (2) for the compounds of the formulas (IV) to (VII) may be likewise used.

The secondary alcohol of the formula (5) is a novel intermediate compound and the preparation thereof is described.

Like the 4-(4-silacyclohexyl)cyclohexylcarboxylic acids set out hereinbefore, the preparation of the secondary alcohol of the formula (5) differs depending on the type thereof.

(A') The preparation of the secondary alcohol of the formula (5) where the substituent is a methyl group, i.e. W, $W^1$ and/or $W^2$ =$CH_3$, is described for different types (a") to (d") of silicon-containing secondary alcohols.

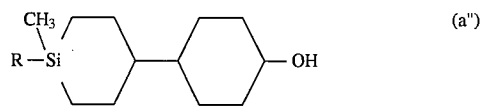 (a")

This compound is prepared during the course of the preparation of a corresponding acid in (a) of (A) set forth hereinbefore (see the reaction sequence (a-2)).

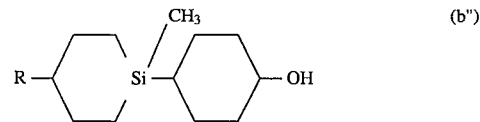 (b")

This type of alcohol is prepared during the course of the preparation of a corresponding acid in (b) of (A) (see the reaction sequence (b-2)).

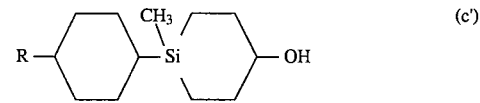 (c')

This type of secondary alcohol is prepared from a silacyclohexanone compound of the following formula (c"-1) by hydrogenation of the aromatic ring and reduction of the ketone

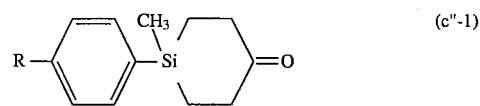 (c"-1)

The reaction sequence is shown below as (c"-2)

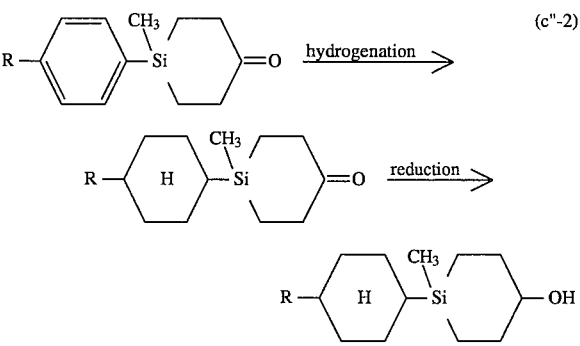 (c"-2)

The hydrogenation of the aromatic ring is carried out in the same manner as in (A) and the reduction of the ketone may be conducted according to any of known procedures as set out hereinbefore.

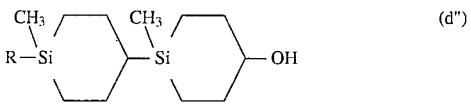

This compound is obtained using the ketone compound shown in the reaction sequence (d-2) of (A) according to the following reaction formula

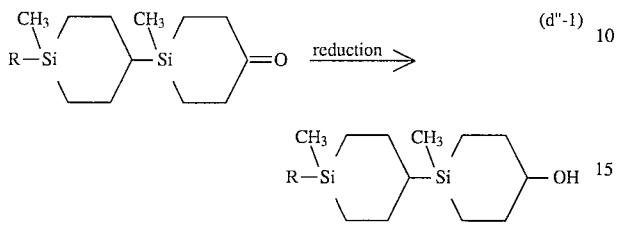

This reduction reaction is carried out by any of known reduction procedures for ketones as set forth hereinbefore.

(B') The preparation of the secondary alcohol of the formula (5) where the substituent is F, Cl or H, i.e. W, $W^1$ and/or $W^2$=F, Cl or H, is described for different types (a''') to (d''') of silacyclohexane-bearing alcohol compounds. It will be noted that because the conversion of an arylsilacyclohexane to chlorosilacyclohexane, fluorosilacyclohexane and hydrosilacyclohexane has been already described hereinbefore, preparation of different types of alcohol compounds of the formula (5) is described below.

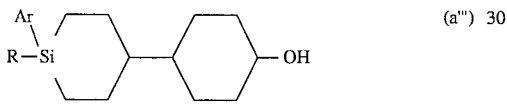

This compound is prepared from a silacyclohexylcyclohexanone by reduction according to the following reaction formula (a'''-1)

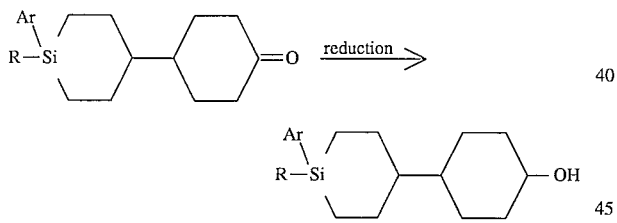

This reduction is feasible in a manner as set out hereinbefore. The preparation of the starting material is set out in Japanese Patent Application No. 6-154219, filed Jun. 13, 1994 and not yet laid open.

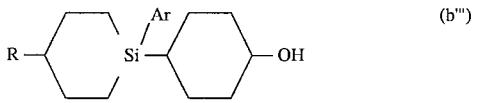

This compound is obtained during the course of preparing a corresponding carboxylic acid as shown hereinbefore in the reaction sequence (b'-2).

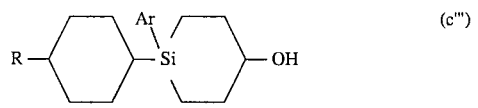

This type of secondary alcohol is prepared from a silacyclohexanone compound of the following formula (c'''-1) by hydrogenation of the aromatic ring and reduction of the ketone

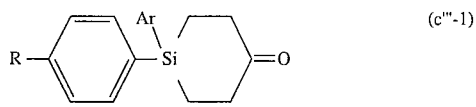

The hydrogenation and reduction are feasible in the same manner as in (c''-2).

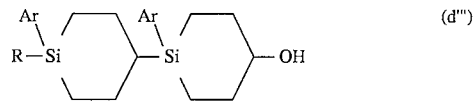

This compound is obtained from the ketone compound shown in the reaction sequence (d'-2) of (A) according to the following reaction formula

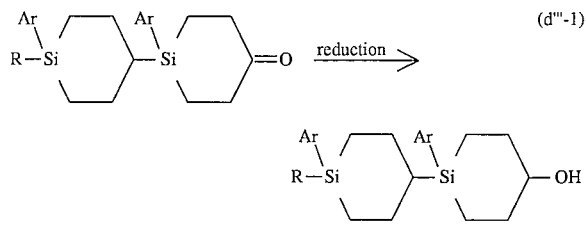

The reduction is effected in the same manner as set out hereinbefore.

The silacyclohexane compounds of the invention are appropriately used in combination with known liquid crystal compounds to provide a liquid crystal composition. Such liquid crystal compounds suitable for this purpose include those compounds of the general formulas (6) and (7)

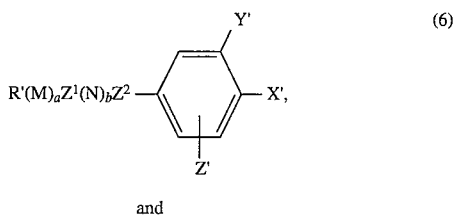

and

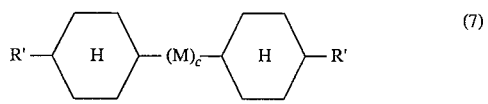

In the above formula (6) and (7), each R' represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms as defined in the afore-indicated formula (I); X' is same as X defined hereinbefore and represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, CHFCl, $OCF_3$, $OCF_2Cl$, OCHFCl, $OCHF_2$, $(O)_lCY=CX_1X_2$ wherein l is 0 or 1, Y and $X_1$ independently represent H, F or Cl, $X_2$ represents H, F or Cl, or $O(CH_2)_r(CF_2)_sX_3$ wherein r and s are, respectively, 0, 1 or 2 provided that r+s=2, 3 or 4, $X_3$ represents H, F or Cl; Y' and Z' independently represent H or F; M and N independently represent (1) an unsubstituted or substituted trans-1,4-cyclohexylene group which has, if substituted, one or more substituents such as F, Cl, Br, CN and an alkyl group having from 1 to 3 carbon atoms, (2) a trans-1,4-cyclohexylene group wherein one $CH_2$ unit or two $CH_2$ units, not adjacent each other, of the cyclohexane ring are replaced by O or S, (3) a 1,4-cyclohexenylene group, (4) an unsubstituted or substituted 1,4-phenylene group having, if substituted, one or two F, Cl, $CH_3$ and/or CN groups and (5) a 1,4-phenylene group in which one or two CH units of the phenylene group are replaced by nitrogen atom, a and b are, respectively, 0, 1 or 2 provided that a+b=1, 2 or 3, and c is 0, 1 or 2; and $Z^1$ and $Z^2$ are, respectively, —$CH_2CH_2$—, —CH=CH—, —C≡C—, —$CO_2$—, —OCO—, —$CH_2O$—, —$OCH_2$— or single bond.

In the above formulas (6) and (7), if a, b and/or c is 2, M's and/or N's may be the same or different and are independently selected from the groups (1) to (5) set forth above.

The silacyclohexane compounds which may be used singly or in combination should preferably be present in a liquid crystal phase or composition in an amount of from 1 to 50 mole %, preferably from 5 to 30 mole %. As a matter of course, the liquid crystal composition may further comprise polychromatic dyes capable of forming colored guest-host systems, and additives capable of imparting dielectric anisotropy, viscosity modifiers, additives for changing the direction of alignment of a nematic phase.

In practice, the liquid crystal phase or composition comprising at least one compound of the invention is used as a liquid crystal display device wherein the composition is hermetically sealed between transparent substrates each having an electrode of a desired shape. If necessary, the device may have various types of undercoatings, an overcoating for controlling the alignment, a polarizer, a filter and a reflective layer as is known in the art. Alternatively, a multi-layer cell may be used to incorporate the compounds of the invention. The liquid crystal display device may be used in combination with other types of display devices, semiconductor substrates, and light sources.

With the compounds of the invention whose value of Δε is positive or is close to zero, the liquid crystal display device is driven according to a twisted nematic (TN) system, a super twisted nematic (STN) system or a guest-host (GH) system. For the compounds whose value of Δε is negative, a dynamics scattering mode (DSM) system, an electrically controlled birefringence(ECB) system, a guest-host (GH) system and the like known in the art may be adopted.

The invention is more particularly described by way of examples.

EXAMPLE 1

Preparation of 4-fluorophenyl trans, trans-4-(4-methyl-4-n-propyl-4-silacyclohexyl)cyclohexanecarboxylate 2.50 g of N,N'-dicyclohexylcarbodiimide (DCC) was added to a mixture of 2.83 g of trans, trans-4-(4-methyl-4-n-propyl-4-silacyclohexyl)cyclohexanecarboxylic acid, 1.30 g of 4-fluorophenol, 1.50 g of 4-dimethylaminopyridine and 30 ml of methylene chloride at room temperature. The resultant reaction mixture was agitated for 8 hours at room temperature, after which the resultant N,N'-dicyclohexyl urea was removed by filtration. The tiltrate was washed with brine, dried and concentrated to obtain a residue, followed by silica gel chromatography to obtain 2.82 g (yield: 75%) of the intended product.

EXAMPLE 2

Preparation of 4-chlorophenyl trans, trans-4-(4-methyl-4-n-pentyl-4-silacyclophexyl)cyclohexanecarboxylate The general procedure of Example 1 was repeated using trans, trans-4-(4-methyl-4-n-pentyl-4-silacyclohexyl)cyclohexanecarboxylic acid and 4-chlorophenol, thereby obtaining the intended product.

EXAMPLE 3

Preparation of 4-n-propylphenyl trans, trans-4-methyl-4-(4-n-pentylcyclohexyl)-4-silacyclohexanercarboxylate The general procedure of Example 1 was repeated using trans, trans-4-methyl-4-(4-n-pentylcyclohexyl)-4-silacyclohexanecarboxylic acid and 4-n-propylphenol, thereby obtaining the intended product.

EXAMPLE 4

Preparation of 4-fluorophenyl trans, trans-4-(4-n-propyl-4-silacyclohexyl)cyclohexanecarboxylate A mixture of 3.58 g of 4-(4-phenyl-4-n-propyl-4-silacyclohexyl)cyclohexanecarboxylic acid, 3.0 g of triphenylphosphine and 50 ml of carbon tetrachloride was agitated under reflux for 6 hours. Then, a mixture of 1.50 g of 4-fluorophenol and 10 ml of pyridine was added to the mixture, followed by further addition of 50 mg of 4-dimethylaminopyridine and agitation at room temperature for 18 hours. The resultant reaction mixture was poured into dilute hydrochloric acid, followed by extraction with ethyl acetate. The ethyl acetate solution was washed with brine, dried and concentrated, followed by purification of the resultant residue with silica gel chromatography to obtain 3.20 g (yield: 70%) of 4-fluorophenyl 4-(4-phenyl-n-propyl-4-silacyclohexyl)cyclohexanecarboxylate. The results of IR and NMR analyses are shown below. IR (KBr, disc) $v_{max}$: 2924, 2856, 1751, 1504, 1190, 1136, 1113, 984, 860 $cm^{-1}$ $^1$H-NMR (CDCl$_3$) δ: 0.6–2.9 (26H, m), 6.9–7.0 (2H, d), 7.0–7.1 (2H, m), 7.3–7.6 (5H, m) ppm 3.5 ml of a carbon tetrachloride solution of 1.0 mole of iodine monochloride was added to a mixture of 1.00 g of the thus obtained product and 15 ml of carbon tetrachloride at room temperature and agitated for 1 hour. The reaction mixture was concentrated under reduced pressure to obtain 805 mg (yield: 96%) of 4-fluorophenyl 4-(4-chloro-n-propyl-4-silacyclohexyl)cyclohexanecarboxylate. The results of gas chromatography-mass spectroscopy (GC-MS) are shown below.

GC-MS (m/z)$^+$: 396, 353, 285, 257, 215, 175

700mg of the thus obtained product was added to a mixture of 200 mg of lithium aluminium hydride and 20 ml of tetrahydrofuran and agitated at −20° C. for 15 minutes. The reaction mixture was poured into dilute sulfuric acid and extracted with methylene chloride. The methylene chloride solution was washed with brine, dried and concentrated, followed by purification through silica gel chromatography to obtain 228 mg (yield: 36%) of the intended product. The results of IR analysis and measurement of phase transition temperatures are shown below.

IR (KBr, disc) $v_{max}$: 2920, 2850, 1749, 1504, 1188, 1134, 989, 887, 837 $cm^{-1}$ $T_{CN}$ (crystal phase-nematic phase transition temperature)=64° C.

$T_{NI}$ (nematic phase-isotropic phase transition temperature)=136° C.

EXAMPLE 5

Preparation of 4-chlorophenyl trans, trans-4-fluoro-(4-(3-methylbutyl)cyclohexyl)-4-silacyclohexanecarboxylate The general procedure of Example 4 was repeated using 4-chlorophenol and 4-phenyl-(4-(3-methylbutyl)cyclohexyl)-4-silacyclohexanecarboxylic acid, thereby obtaining the intended product.

EXAMPLE 6

Preparation of 4-cyanophenyl trans, trans-4-(4-n-pentyl-4-silacyclohexyl)cyclohexanecarboxylate The general procedure of Example 4 was repeated using 4-cyanophenol and 4-(4-phenyl-4-n-pentyl-4-silacyclohexyl)cyclohexanecarboxylic acid, thereby obtaining the intended product.

EXAMPLE 7

Preparation of 4-fluorophenyl trans, trans-4-(4-n-pentyl-4-silacyclohexyl)cyclohexanecarboxylate The general procedure of Example 4 was repeated using 4-(4-phenyl-4-n-pentyl-4-silacyclohexyl)cyclohexanecarboxylic acid, thereby obtaining the intended product.

EXAMPLE 8

Preparation of 4-chlorophenyl trans, trans-4-(4-n-propyl-4-silacyclohexyl)cyclohexanecarboxylate The general procedure of Example 4 was repeated using 4-chlorophenol, thereby obtaining the intended product. The results of IR analysis and measurement of phase transition temperatures are shown below.

IR (KBr, disc) $v_{max}$: 2920, 2850, 2102, 1749, 1487, 1198, 1138, 987, 887, 837 cm$^{-1}$ $T_{CN}$ (crystal phase-nematic phase transition temperature)=83° C.

$T_{NI}$ (nematic phase-isotropic phase transition temperature)=171° C.

EXAMPLE 9

Preparation of 4-trifluoromethoxyphenyl trans, trans-4-(4-n-propyl-4-silacyclohexyl)cyclohexanecarboxylate The general procedure of Example 4 was repeated using 4-trifluoromethoxyphenol, thereby obtaining the intended product. The results of IR analysis and measurement of phase transition temperatures are shown below.

IR (KBr, disc) $v_{max}$: 2927, 2854, 2102, 1757, 1504, 1282, 1223, 1167, 1138, 989, 887, 845 cm$^{-1}$ $T_{SN}$ (smectic phase-nematic phase transition temperature)=107° C.

$T_{NI}$ (nematic phase-isotropic phase transition temperature)=148° C.

EXAMPLE 10

Preparation of 4-n-pentylphenyl trans, trans-4-(4-n-propyl-4-silacyclohexyl)cyclohexanecarboxylate The general procedure of Example 4 was repeated using 4-n-pentylphenol, thereby obtaining the intended product. The results of IR analysis and measurement of phase transition temperatures are shown below.

IR (KBr, disc) $v_{max}$: 2924, 2854, 2096, 1749, 1508, 1200, 1165, 1138, 1115, 987, 887, 843, 818 cm$^{-1}$ $T_{CS}$ (crystal phase-smectic phase transition temperature)=43° C.

$T_{SN}$ (smectic phase-nematic phase transition temperature)=127° C.

$T_{NI}$ (nematic phase-isotropic phase transition temperature)=151° C.

EXAMPLE 11

Preparation of 3,4-difluorophenyl trans, trans-4-(4-n-propyl-4-silacyclohexyl)cyclohexanecarboxylate The general procedure of Example 4 was repeated using 3,4-difluorophenol, thereby obtaining the intended product. The results of IR analysis and measurement of phase transition temperatures are shown below.

IR (KBr, disc) $v_{max}$: 2926, 2852, 2108, 1757, 1514, 1261, 1196, 1144, 1107, 989, 835, 795 cm$^{-1}$ $T_{CN}$ (crystal phase-nematic phase transition temperature)=38° C.

$T_{NI}$ (nematic phase-isotropic phase transition temperature)=50° C.

EXAMPLE 12

Preparation of 4-cyano-3-fluorophenyl trans, trans-4-(4-n-propyl-4-silacyclohexyl)cyclohexanecarboxylate The general procedure of Example 4 was repeated using 4-cyano-3-fluorophenol, thereby obtaining the intended product.

EXAMPLE 13

Preparation of 4-chloro-3-fluorophenyl trans, trans-4-(4-n-pentyl-4-silacyclohexyl)cyclohexanecarboxylate The general procedure of Example 4 was repeated using 4-chloro-3-fluorophenol and 4-fluoro-(4-phenyl-4-n-pentyl-4-silacyclohexyl)cyclohexanecarboxylic acid, thereby obtaining the intended product.

EXAMPLE 14

Preparation of 4-chloro-3-methylphenyl trans, trans-4-(4-n-propyl-4-silacyclohexyl)cyclohexanecarboxylate The general procedure of Example 4 was repeated using 4-chloro-3-methylphenol, thereby obtaining the intended product.

EXAMPLE 15

Preparation of 3,4,5-trifluorophenyl trans, trans-4-(4-n-pentyl-4-silacyclohexyl)cyclohexanecarboxylate The general procedure of Example 4 was repeated using 3,4,5-trifluorophenol and 4-(4-phenyl-4-n-pentyl-4-silacyclohexyl)cyclohexanecarboxylic acid, thereby obtaining the intended product.

EXAMPLE 16

Preparation of 3,5-difluoro-4-difluoromethoxyphenyl trans, trans-4-(4-n-pentyl-4-silacyclohexyl)cyclohexanecarboxylate The general procedure of Example 4 was repeated using 3,5-difluoro-4-difluoromethoxyphenol and 4-fluoro-(4-phenyl-4-n-pentyl-4-silacyclohexyl)cyclohexanecarboxylic acid, thereby obtaining the intended product.

EXAMPLE 17

Preparation of 4-ethoxy-2,3-difluorophenyl trans, trans-4-(4-n-propyl-4-silacyclohexyl)cyclohexanecarboxylate The general procedure of Example 4 was repeated using 4-ethoxy-2,3-difluorophenol, thereby obtaining the intended product.

EXAMPLE 18

Preparation of 4-methoxyphenyl trans, trans-4-(4-n-butyl-4-silacyclohexyl)cyclohexanecarboxylate The general procedure of Example 4 was repeated using 4-methoxyphenol and 4-(4-phenyl-4-n-butyl-4-silacyclohexyl)cyclohexanecarboxylic acid, thereby obtaining the intended product.

EXAMPLE 19

Preparation of 3,4-dichlorophenyl trans, trans-4-(4-(5-methoxypentyl)-4-silacyclohexyl)cyclohexanecarboxylate The general procedure of Example 4 was repeated using 3,4-dichlorophenol and 4-(4-phenyl-4-(5-methoxypentyl)-4-silacyclohexyl)cyclohexanecarboxylic acid, thereby obtaining the intended product.

EXAMPLE 20

Preparation of 4-chloro-2-fluorophenyl trans, trans-4-(4-(4-pentenyl)-4-silacyclohexyl)cyclohexanecarboxylate The general procedure of Example 4 was repeated using 4-chloro-2-fluorophenol and 4-(4-phenyl-4-(4-pentenyl)-4-silacyclohexyl)cyclohexanecarboxylic acid, thereby obtaining the intended product.

EXAMPLE 21

Preparation of 4-trifluoromethylphenyl trans, trans-4-(4-(3-methylbutyl)-4-silacyclohexyl)cyclohexanecarboxylate The general procedure of Example 4 was repeated using 4-trifluoromethylphenol and 4-(4-phenyl-4-(4-methylbutyl)-4-silacyclohexyl)cyclohexanecarboxylic acid, thereby obtaining the intended product.

EXAMPLE 22

Preparation of 4-fluorophenyl trans, trans-4-(4-(5-methoxypentyl)cyclohexyl)-4-silacyclohexanecarboxylate The general procedure of Example 4 was repeated using 4-(4-phenyl-4-(5-methoxypentyl)cyclohexyl)-4-silacyclohexanecarboxylic acid, thereby obtaining the intended product.

EXAMPLE 23

Preparation of 3,4-difluorophenyl trans, trans-4-(4-(4-pentenyl)cyclohexyl)-4-silacyclohexanecarboxylate The general procedure of Example 4 was repeated using 3,4-difluorophenol and 4-(4-phenyl-4-(4-pentenyl)cyclohexyl)-4-silacyclohexanecarboxylic acid, thereby obtaining the intended product.

EXAMPLE 24

Preparation of 4-trifluoromethoxyphenyl trans, trans-4-(4-n-pentylcyclohexyl)-4-silacyclohexanecarboxylate The general procedure of Example 4 was repeated using 4-trifluoromethoxyphenol and 4-(4-phenyl-4-(4-pentyl)cyclohexyl)-4-silacyclohexanecarboxylic acid, thereby obtaining the intended product.

EXAMPLE 25

Preparation of 4-cyanophenyl trans, trans-4-(4-n-pentyl-4-silacyclohexyl)-4-silacyclohexanecarboxylate The general procedure of Example 4 was repeated using 4-cyanophenol and 4-(phenyl)-(4-phenyl-4-pentyl-4-silacyclohexyl)-4-silacyclohexanecarboxylic acid, thereby obtaining the intended product.

EXAMPLE 26

Preparation of 4-(3-methoxypropyl)phenyl trans, trans-4-(4-n-propyl-4-silacyclohexyl)- 4-cyclohexanecarboxylate The general procedure of Example 4 was repeated using 4-(3-methoxypropyl)phenol and 4-(4-phenyl-4-propyl-4-silacyclohexyl)-4-cyclohexanecarboxylic acid, thereby obtaining the intended product.

EXAMPLE 27

A liquid crystal mixture was prepared by mixing 20% by mole of trans-4-(2-(3,4-difluorophenyl)ethyl)-1-butylcyclohexane, 32% by mole of 4-(trans-4-(trans-4-ethylcyclohexyl)cyclohexyl)-1,2-difluorobenzene, 28% by mole of 4-(trans-4-(trans-4-n-propylcyclohexyl)cyclohexyl)-1,2-difluorobenzene, and 20% by mole of 4-(trans-4-(trans-4-n-pentylcyclohexyl)cyclohexyl)-1,2-difluorobenzene. The mixture had the following phase transition temperatures.

$T_{CN}$ (crystal phase-nematic phase transition temperature)=−1° C.

$T_{NI}$ (nematic phase-isotropic phase transition temperature)=75° C.

85% by mole of the mixture was further mixed with 15% by mole of (4-fluorophenyl) trans, trans-4-(4-n-propyl-4-silacyclohexyl)cyclohexanecarboxylate. The resultant mixture exhibited a nematic-isotropic phase transition temperature shifted to a higher temperature region as shown below.

$T_{CN}$ (crystal phase-nematic phase transition temperature)=−6° C.

$T_{NI}$ (nematic phase-isotropic phase transition temperature)=86° C.

EXAMPLE 28

Preparation of trans, trans-(4-(4-methyl-4-n-propyl-4-silacyclohexyl)cyclohexyl) 4-fluorobenzoate 2.50 g of N,N'-dicyclohexylcarbodiimide (DCC) was added to a mixture of 1.80 g of 4-fluorobenzoic acid, 2.54 g of trans-4-(4-methyl-4-n-propyl-4-silacyclohexyl)cyclohexanol, 1.50 g of 4-dimethylaminopyridine and 30 ml of methylene chloride at room temperature. The resultant reaction mixture was agitated for 8 hours at room temperature, after which the resultant N,N'-dicyclohexyl urea was removed by filtration. The filtrate was washed with brine, dried and concentrated to obtain a residue, followed by silica gel chromatography to obtain 2.12 g (yield: 56%) of the intended product.

EXAMPLE 29

Preparation of trans, trans-4-(4-methyl-4-n-pentyl-4-silacyclohexyl)cyclohexyl) 4-chlorobenzoate The general procedure of Example 28 was repeated using trans, trans-4-(4-methyl-4-n-pentyl-4-silacyclohexyl)cyclohexanol and 4-chlorobenzoic acid, thereby obtaining the intended product.

EXAMPLE 30

Preparation of trans, trans-(4-methyl-4-(4-n-pentylcyclohexyl)-4-silacylohexyl) 4-n-propylbenzoate The general procedure of Example 28 was repeated using trans, trans-(4-methyl-4-(4-n-pentylcyclohexyl)-4-silacyclohexanol and 4-n-propylbenzoic acid, thereby obtaining the intended product.

EXAMPLE 31

Preparation of trans, trans-(4-(4-n-propyl-4-silacylohexyl) cyclohexyl) 4-trifluoromethoxybenzoate 30.9 g of 4-trifluoromethoxybenzoyl chloride was dropped in a mixture of 31.7 g of 4-(4-phenyl-4-n-propyl-4-silacyclohexyl)cyclohexanol, 150 ml of pyridine and 100 mg of 4-dimethylaminopyridine, followed by agitation at room temperature for 10 hours. Thereafter, the reaction mixture was charged into dilute hydrochloric acid and extracted with ethyl acetate. The ethyl acetate solution was washed with brine, dried and concentrated, followed by purification of the resultant residue through silica gel chromatography to obtain 35.8 g (yield: 71%) of 4-(4-(phenyl-4-n-propyl-4-silacyclohexyl)cyclohexyl) 4-trifluoromethoxybenzoate. The results of IR and NMR analyses are shown below.

IR (KBr, disc) $v_{max}$: 2927, 2862, 1718, 1608, 1506, 1259, 1215, 1169, 1111, 987, 858 cm$^{-1}$ $^1$H-NMR (CDCl$_3$) δ: 0.7–2.3 (26H, m), 7.1–7.6 (7H, m), 8.0–8.3.1 (2H, m) ppm 25 ml of a carbon tetrachloride solution of 1.0 mole of iodine monochloride was added to a mixture of 10.0 g of the thus obtained product and 150 ml of carbon tetrachloride at room temperature and agitated for 1 hour. The reaction mixture was concentrated under reduced pressure to obtain crude 4-(4-chloro-n-propyl-4-silacyclohexyl)cyclohexyl 4-fluoromethoxybenzoate.

The thus obtained product was added to a mixture of 400 mg of lithium aluminium hydride and 50 ml of diethyl ether at −40° C., followed by agitation at −40° C. for 25 minutes. The reaction mixture was poured into dilute sulfuric acid and extracted with methylene chloride. The methylene chloride solution was washed with brine, dried and concentrated, followed by purification through silica gel chromatography to obtain 3.40 g (yield: 40%) of the intended product. The results of IR analysis and measurement of phase transition temperatures are shown below.

IR (KBr, disc) $v_{max}$: 2927, 2858, 2104, 1718, 1608, 1506, 1267, 1215, 1167, 1122, 991, 887 cm$^{-1}$ $T_{CN}$ (crystal phase-smectic phase transition temperature)=59.6° C.

$T_{SN}$ (smectic phase-nematic phase transition temperature)=117.6° C. $T_{NI}$ (nematic phase-isotropic phase transition temperature)=137.1° C.

EXAMPLE 32

Preparation of trans, trans-(4-fluoro-4-(4-(3-methylbutylcyclohexyl)cyclohexyl)-4-silacyclohexyl) 4-chlorobenzoate The general procedure of Example 31 was repeated using 4-chlorobenzoic acid and 4-phenyl-4-(4-(3-methylbutyl)cyclohexyl)-4-silacyclohxanol, thereby obtaining the intended product.

EXAMPLE 33

Preparation of trans, trans-(4-(4-n-pentyl-4-silacyclohexyl) cyclohexyl) 4-fluorobenzoate The general procedure of Example 31 was repeated using 4-(4-phenyl-4-n-pentyl-4-silacyclohexyl)cyclohexanol, thereby obtaining the intended product.

EXAMPLE 34

Preparation of trans, trans-(4-(4-n-propyl-4-silacyclohexyl) cyclohexyl) 4-cyanobenzoate The general procedure of Example 31 was repeated using 4-cyanobenzoic acid, thereby obtaining the intended product.

EXAMPLE 35

Preparation of trans, trans-(4-(4-n-propyl-4-silacyclohexyl) cyclohexyl) 4-chlorobenzoate The general procedure of Example 31 was repeated using 4-chlorobenzoic acid, thereby obtaining the intended product. The results of IR analysis and measurement of phase transition temperatures are shown below.

IR (KBr, disc) $v_{max}$: 2918, 2858, 2104, 1713, 1593, 1487, 1290, 1128, 989, 885, 827 cm$^{-1}$ $T_{CN}$ (crystal phase-nematic phase transition temperature)=95.9° C.

$T_{NI}$ (nematic phase-isotropic phase transition temperature)=166.4° C.

EXAMPLE 36

Preparation of trans, trans-(4-(4-n-propyl-4-silacyclohexyl) cyclohexyl) 4-fluorobenzoate The general procedure of Example 31 was repeated using 4-fluorobenzoic acid, thereby obtaining the intended product. The results of IR analysis and measurement of phase transition temperatures are shown below.

IR (KBr, disc) $v_{max}$: 2924, 2862, 2104, 1718, 1603, 1506, 1279, 989, 887, 852 cm$^{-1}$ $T_{CN}$ (crystal phase-nematic phase transition temperature)=67.6° C.

$T_{NI}$ (nematic phase-isotropic phase transition temperature)=137.2° C.

EXAMPLE 37

Preparation of trans, trans-(4-(4-n-propyl-4-silacyclohexyl) cyclohexyl) 4-pentylbenzoate The general procedure of Example 31 was repeated using 4-pentylbenzoic acid, thereby obtaining the intended product. The results of IR analysis and measurement of phase transition temperatures are shown below.

IR (KBr, disc) $v_{max}$: 2926, 2858, 2114, 1711, 1610, 1450, 1277, 1107, 991, 891 cm$^{-1}$ $T_{CN}$ (crystal phase-nematic phase transition temperature)=49.6° C.

$T_{NI}$ (nematic phase-isotropic phase transition temperature)=123.6° C.

EXAMPLE 38

Preparation of trans, trans-(4-(4-n-propyl-4-silacyclohexyl) cyclohexyl) 3,4-difluorobenzoate The general procedure of Example 31 was repeated using 3,4-difluorobenzoic acid, thereby obtaining the intended product. The results of IR analysis and measurement of phase transition temperatures are shown below.

IR (KBr, disc) $v_{max}$: 2920, 2860, 2094, 1714, 1610, 1514, 1431, 1290, 991, 889 cm$^{-1}$ $T_{CN}$ (crystal phase-nematic phase transition temperature)=66.6° C.

$T_{NI}$ (nematic phase-isotropic phase transition temperature)=118.5° C.

EXAMPLE 39

Preparation of trans, trans-(4-(4-n-propyl-4-silacyclohexyl) cyclohexyl) 4-cyano-3-fluorobenzoate The general procedure of Example 31 was repeated using 4-cyano-3-fluorobenzoic acid, thereby obtaining the intended product.

EXAMPLE 40

Preparation of trans, trans-(4-(4-n-propyl-4-silacyclohexyl)cyclohexyl) 4-chloro-3-flurobenzoate The general procedure of Example 31 was repeated using 4-chloro-3-fluorobenzoic acid, thereby obtaining the intended product.

EXAMPLE 41

Preparation of trans, trans-(4-(4-n-propyl-4-silacyclohexyl)cyclohexyl) 4-chloro-3-methylbenzoate The general procedure of Example 31 was repeated using 4-chloro-3-methylbenzoic acid, thereby obtaining the intended product.

EXAMPLE 42

Preparation of trans, trans-(4-(4-n-propyl-4-silacyclohexyl)cyclohexyl) 3,4,5-trifluorobenzoate The general procedure of Example 31 was repeated using 3,4,5-trifluorobenzoic acid, thereby obtaining the intended product.

EXAMPLE 43

Preparation of trans, trans-(4-(4-n-propyl-4-silacyclohexyl)cyclohexyl) 3,5-difluoro-4-difluoromethoxybenzoate The general procedure of Example 31 was repeated using 3,5-difluoro-4-difluoromethoxybenzoic acid, thereby obtaining the intended product.

EXAMPLE 44

Preparation of trans, trans-(4-(4-n-butyl-4-silacyclohexyl)cyclohexyl) 4-ethoxy-2,3-difluorobenzoate The general procedure of Example 31 was repeated using 4-ethoxy-2,3-difluorobenzoic acid and 4-(4-phenyl-4-n-butyl-4-silacyclohexyl)cyclohexanol, thereby obtaining the intended product.

EXAMPLE 45

Preparation of trans, trans-(4-(4-n-butyl-4-silacyclohexyl)cyclohexyl) 4-methoxybenzoate The general procedure of Example 31 was repeated using 4-methoxybenzoic acid and 4-(4-phenyl-4-n-butyl-4-silacyclohexyl)cyclohexanol, thereby obtaining the intended product.

EXAMPLE 46

Preparation of trans, trans-(4-(4-(5-methoxypentyl)-4-silacyclohexyl)cyclohexyl) 3,4-dichlorobenzoate The general procedure of Example 31 was repeated using 3,4-dichlorobenzoic acid and 4-(4-phenyl-4-(4-methoxypentyl)-4-silacyclohexyl)cyclohexanol, thereby obtaining the intended product.

EXAMPLE 47

Preparation of trans, trans-(4-(4-(4-pentenyl)-4-silacyclohexyl)cyclohexyl) 4-chloro-2-fluorobenzoate The general procedure of Example 31 was repeated using 4-chloro-2-fluorobenzoic acid and 4-(4-phenyl-(3-pentenyl)-4-silacyclohexyl)cyclohexanol, thereby obtaining the intended product.

EXAMPLE 48

Preparation of trans, trans-(4-(4-(3-methylbutyl)-4-silacyclohexyl)cyclohexyl) 4-trifluoromethylbenzoate The general procedure of Example 31 was repeated using 4-trifluoromethylbenzoic acid and 4-(4-phenyl-(4-(30-methylbutyl)-4-silacyclohexyl)cyclohexanol, thereby obtaining the intended product.

EXAMPLE 49

Preparation of trans, trans-(4-(4-(5-methoxypentyl)cyclohexyl)-4-silacyclohexyl) 4-fluorobenzoate The general procedure of Example 31 was repeated using 4-fluorobenzoic acid and 4-(4-(5-methoxypentyl)cyclohexyl)-4-silacyclohexanol, thereby obtaining the intended product.

EXAMPLE 50

Preparation of trans, trans-(4-(4-(5-pentenyl)cyclohexyl)-4-silacyclohexyl) 3,4-difluorobenzoate The general procedure of Example 31 was repeated using 3,4-difluorobenzoic acid and 4-(4-(5-pentenyl)cyclohexyl)-4-silacyclohexanol, thereby obtaining the intended product.

EXAMPLE 51

Preparation of trans, trans-(4-(4-n-pentylcyclohexyl)-4-silacyclohexyl) 4-trifluoromethoxybenzoate The general procedure of Example 31 was repeated using 4-trifluoromethoxybenzoic acid and 4-(4-n-pentylcyclohexyl)-4-silacyclohexanol, thereby obtaining the intended product.

EXAMPLE 52

Preparation of trans, trans-(4-(4-n-pentyl-4-silacyclohexyl)-4-silacyclohexyl) 4-cyanobenzoate The general procedure of Example 31 was repeated using 4-cyanobenzoic acid and 4-(4-phenyl-4-n-pentyl-4-silacyclohexyl)-4-silacyclohexanol, thereby obtaining the intended product.

EXAMPLE 53

Preparation of trans, trans-(4-(4-n-propyl-4-silacyclohexyl)cyclohexyl) 4-(3-methoxypropyl)benzoate The general procedure of Example 31 was repeated using 4-(3-methoxypropyl)benzoic acid, thereby obtaining the intended product.

EXAMPLE 54

Preparation of trans, trans-(4-(4-(4-fluorobutyl)-4-silacyclohexyl)cyclohexyl) 4-trifluoromethoxybenzoate The general procedure of Example 31 was repeated using 4-trifluoromethoxybenzoic acid and 4-(4-phenyl-4-fluorobutyl)-4-silacyclohexyl)cyclohexanol, thereby obtaining the intended product.

EXAMPLE 55

As in Example 27, a liquid crystal mixture was prepared by mixing 20% by mole of trans-4-(2-(3,4-difluorophenyl)ethyl)-1-butylcyclohexane, 32% by mole of 4-(trans-4-(trans-4-ethylcyclohexyl)[cyclohexyl]]cyclohexyl)-1,2-difluorobenzene, 28% by mole of 4-(trans-4-(trans-4-n-propylcyclohexyl)-1,2-difluorobenzene, and 20% by mole of 4-(trans-4-(trans-4-n-pentylcyclohexyl)cyclohexyl)-1,2-difluorobenzene. The mixture had the following phase transition temperatures.

$T_{NI}$ (nematic phase-isotropic phase transition temperature)=75° C.

$T_{CN}$ (crystal phase phase-nematic phase transition temperature)=–0.5° C.

80% by mole of the mixture was further mixed with 20% by mole of (4-(4-n-propyl-4-silacylohexyl)cyclohexyl) 4-fluorobenzoate. The resultant mixture exhibited a nematic-isotropic phase transition temperature shifted to a higher temperature region as shown below.

$T_{NI}$ (nematic phase-isotropic phase transition temperature)=87° C.

$T_{CN}$ (crystal phase-nematic phase transition temperature)=–7° C.

As will be apparent from the foregoing examples, the novel compounds of the invention exhibit relatively high $T_{NI}$ (nematic-isotropic phase transition temperature) without any significant increase in viscosity of a mixed liquid crystal composition comprising the novel compound. Since the $T_{NI}$ is high, the liquid crystal composition can work at a higher temperature and can be used in various fields such as of on-vehicle liquid crystal panels.

What is claimed is:

1. A silacyclohexane compound of the following formula (I)

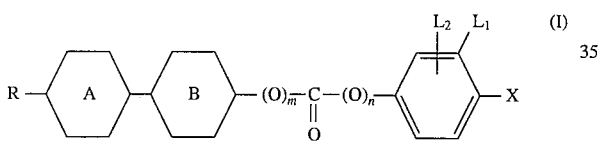

wherein R represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms; at least one of

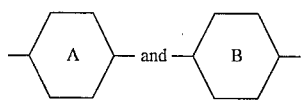

represents a trans-1-sila-1,4-cyclohexylene group or trans-4-sila-1,4-cyclohexylene group in which the silicon atom at the 1 or 4 position has a substituent of H, F, Cl or $CH_3$, and the other represents a trans-1,4-cyclohexylene group, $L_1$ and $L_2$ independently represent H, F, Cl or $CH_3$; X represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY=CX_1X_2$ wherein l is 0 or 1, Y and $X_1$ independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents H, F or Cl; and m and n are, respectively, 0 or 1 provided that m+n=1.

2. A silacyclohexane compound according to claim 1, wherein said compound is of the general formula (II)

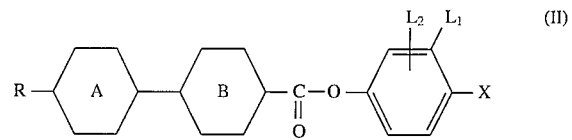

wherein R, X, $L_1$, $L_2$,

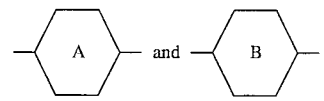

have, respectively, the same meanings as defined in claim 1.

3. A silacyclohexane compound according to claim 2, wherein said compound is of the following formula

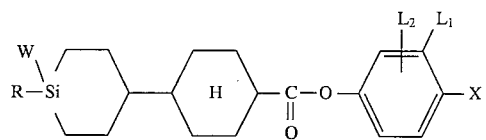

wherein W represents H, F, Cl or $CH_3$.

4. A silacyclohexane compound according to claim 2, wherein said compound is of the following formula

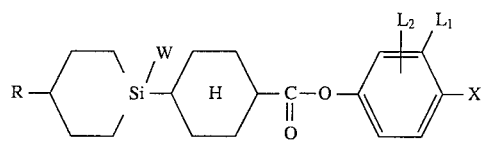

wherein W represents H, F, Cl or $CH_3$.

5. A silacyclohexane compound according to claim 2, wherein said compound is of the following formula

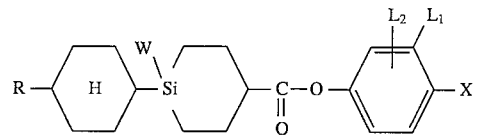

wherein W represents H, F, Cl or $CH_3$.

6. A silacyclohexane compound according to claim 2, wherein said compound is of the following formula

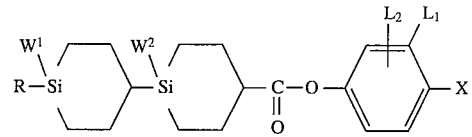

wherein $W_1$ and $W_2$ independently represent H, F, Cl or $CH_3$.

7. A silacyclohexane compound according to claim 1, wherein said compound is of the following formula (III)

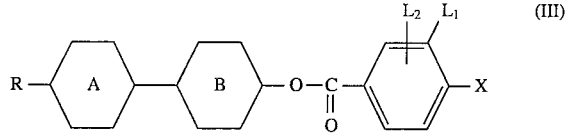

wherein R, X, $L_1$, $L_2$,

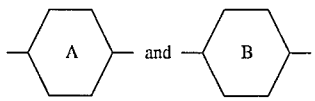

have, respectively, the same meanings as defined in claim 1.

8. A silacyclohexane compound according to claim 7, wherein said compound is of the following formula

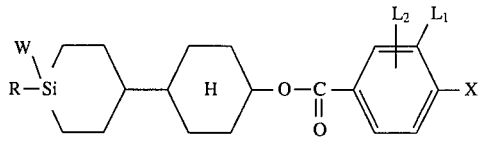

wherein W represents H, F, Cl or $CH_3$.

9. A silacyclohexane compound according to claim 7, wherein said compound is of the following formula

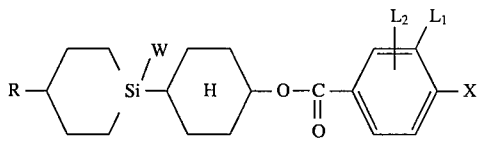

wherein W represents H, F, Cl or $CH_3$.

10. A silacyclohexane compound according to claim 7, wherein said compound is of the following formula

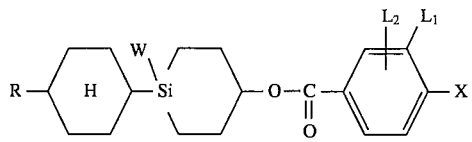

wherein W represents H, F, Cl or $CH_3$.

11. A silacyclohexane compound according to claim 7, wherein said compound is of the following formula

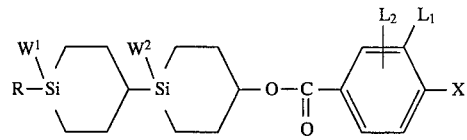

wherein $W_1$ and $W_2$ independently represent H, F, Cl or $CH_3$.

12. A liquid crystal composition comprising at least one silacyclohexane compound of the following formula (I)

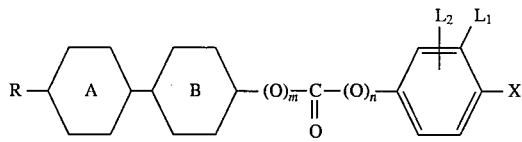

wherein R represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms; at least one of

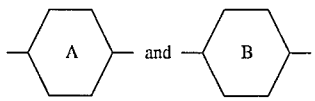

represents a trans-1-sila-1,4-cyclohexylene group or trans-4-sila-1,4-cyclohexylene group in which the silicon atom at the 1 or 4 position has a substituent of H, F, Cl or $CH_3$, and the other represents a trans-1,4-cyclohexylene group, $L_1$ and $L_2$ independently represent H, F, Cl or $CH_3$; X represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY=CX_1X_2$ wherein l is 0 or 1, Y and $X_1$ independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents H, F or Cl; and m and n are, respectively, 0 or 1 provided that m+n=1.

13. A liquid crystal composition according to claim 12, wherein said at least one silacyclohexane compound is present in an amount of from 1 to 50% by mole.

14. A liquid crystal composition according to claim 12, further comprising at least one compound selected from the group consisting of compounds of the following formulas

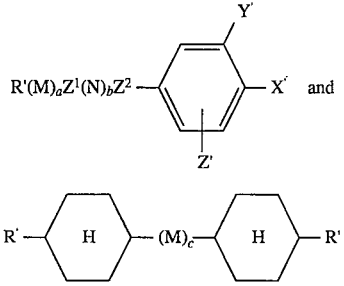

wherein each R' represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms as defined in the afore-indicated formula (I); X' represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY=CX_1X_2$ wherein l is 0 or 1, Y and $X_1$ independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents H, F or Cl; Y' and Z' independently represent H or F; M and N independently represent (1) an unsubstituted or substituted trans-1,4-cyclohexylene group, (2) a trans-1,4-cyclohexylene group wherein one $CH_2$ unit or two $CH_2$ units, which are not adjacent to each other, of the cyclohexane ring are replaced by O or S, (3) a 1,4-cyclohexylene group, (4) an unsubstituted or substituted 1,4-phenylene group and (5) a 1,4-phenylene group in which one or two CH units of the phenylene group are replaced by nitrogen atom, a and b are, respectively, 0, 1 or 2 provided that a+b=1, 2 or 3, and c is 0, 1 or 2; and $Z^1$ and $Z^2$ are, respectively, $-CH_2CH_2-$, $-CH=CH-$, $-C\equiv C-$, $-CO_2-$, $-OCO-$, $-CH_2O-$, $-OCH_2-$ or single bond.

15. A liquid crystal display device comprising the composition defined in claim 12.

* * * * *